US008598134B2

(12) United States Patent
Barik

(10) Patent No.: US 8,598,134 B2
(45) Date of Patent: *Dec. 3, 2013

(54) RNAI MODULATION OF RSV, PIV AND OTHER RESPIRATORY VIRUSES AND USES THEREOF

(75) Inventor: Sailen Barik, Mobile, AL (US)

(73) Assignee: South Alabama Medical Science Foundation, Mobile, AL (US)

(*) Notice: Subject to any disclaimer, the term of this patent is extended or adjusted under 35 U.S.C. 154(b) by 412 days.

This patent is subject to a terminal disclaimer.

(21) Appl. No.: 12/842,878

(22) Filed: Jul. 23, 2010

(65) Prior Publication Data

US 2011/0021606 A1    Jan. 27, 2011

Related U.S. Application Data

(62) Division of application No. 12/492,036, filed on Jun. 25, 2009, now Pat. No. 7,790,878, which is a division of application No. 11/151,976, filed on Jun. 14, 2005, now abandoned.

(60) Provisional application No. 60/621,552, filed on Oct. 22, 2004.

(51) Int. Cl.
*C12N 15/11* (2006.01)
*C07H 21/02* (2006.01)

(52) U.S. Cl.
USPC ............................................ 514/44; 536/24.5

(58) Field of Classification Search
None
See application file for complete search history.

(56) References Cited

U.S. PATENT DOCUMENTS

| | | | |
|---|---|---|---|
| 4,501,729 A | 2/1985 | Boucher et al. | |
| 5,693,532 A | 12/1997 | McSwiggen et al. | |
| 6,107,094 A | 8/2000 | Crooke | |
| 6,214,805 B1 | 4/2001 | Torrence et al. | |
| 6,506,559 B1 | 1/2003 | Fire et al. | |
| 7,427,605 B2 | 9/2008 | Davis et al. | |
| 7,592,322 B2 | 9/2009 | Barik | |
| 7,718,629 B2 | 5/2010 | Bumcrot et al. | |
| 2003/0105051 A1 | 6/2003 | McSwiggen | |
| 2003/0143732 A1 | 7/2003 | Fosnaugh et al. | |
| 2003/0148928 A1 | 8/2003 | Beigelman et al. | |
| 2003/0170891 A1 | 9/2003 | McSwiggen | |
| 2003/0203356 A1 | 10/2003 | Silverman et al. | |
| 2003/0203868 A1 | 10/2003 | Bushman et al. | |
| 2004/0204420 A1 | 10/2004 | Rana | |
| 2004/0242518 A1 | 12/2004 | Chen et al. | |
| 2004/0259247 A1* | 12/2004 | Tuschl et al. ................ | 435/375 |
| 2005/0107325 A1 | 5/2005 | Manoharan et al. | |
| 2006/0084620 A1 | 4/2006 | McCray et al. | |
| 2006/0263435 A1 | 11/2006 | Davis et al. | |
| 2007/0004664 A1 | 1/2007 | McSwiggen et al. | |
| 2007/0031844 A1 | 2/2007 | Khvorova et al. | |
| 2007/0281899 A1 | 12/2007 | Bumcrot et al. | |
| 2009/0149403 A1 | 6/2009 | MacLachlan | |
| 2011/0015250 A1 | 1/2011 | Bumcrot et al. | |

FOREIGN PATENT DOCUMENTS

| | | |
|---|---|---|
| CA | 2 548 150 A1 | 6/2005 |
| WO | WO 97/14792 | 4/1997 |
| WO | WO 2004/028471 | 4/2004 |
| WO | WO 2004/042024 | 5/2004 |
| WO | WO 2004/064737 | 8/2004 |
| WO | WO 2004/065546 | 8/2004 |
| WO | WO 2004/080406 | 9/2004 |
| WO | WO 2004/090108 | 10/2004 |
| WO | WO 2004/094345 | 11/2004 |
| WO | WO 2004/094595 | 11/2004 |
| WO | WO 2005/056021 A1 | 6/2005 |

OTHER PUBLICATIONS

Communication pursuant to Article 94(3) EPC, mailed Apr. 15, 2011, for European Patent Application No. EP 05815963, 4 pages.
Office Action mailed Aug. 15, 2011, for Canadian Patent Application No. CA 2,584,309, 4 pages.
Notification of Reasons for Rejection mailed Nov. 7, 2011, Japanese Patent Application No. JP 2007-538147, 6 pages.
Notice of Preliminary Rejection mailed Dec. 29, 2011, Korean Patent Application No. 10-2007-70115539 Pages.
Reynolds, et al. (2004) "Rational siRNA design for RNA interference," Nature Biotechnology, vol. 22, No. 3, pp. 326-330.
Robbins, M., et al., "Stable expression of shRNAs in human CD34+ progenitor cells can avoid induction of interferon responses to siRNAs in vitro," Nature Biotechnology, May 2006, pp. 566-571, vol. 24, No. 5.
Rose, S., et al., "Functional polarity is introduced by Dicer processing of short substrate RNAs," Nucleic Acids Research, 2005, pp. 4140-4156, vol. 33, No. 13.
Weil, et al (2002) "Targeting the Kinesin Eg5 to Monitor siRNA Transfection in Mammalian Cells," *Biotechniques* 33(6):1244-1248.
Zimmerman, et al. (2006) "RNAi-mediated gene silencing in non-human primates," *Nature*, vol. 441, May 4: 111-114.
Agrawal, et al., "*Antisense therapeutics: is it as simple as complementary base recognition?*" Mol. Med. Today 6:72-81 (2000).
Australian Patent Office Written Opinion, Singapore Patent Application No. 200702872-3, Apr. 23, 2008.
Barik, S., "Control of nonsegmented negative-strand RNA virus replication by siRNA" *Virus Research* 102:27-35 (2004).

(Continued)

*Primary Examiner* — Richard Schnizer
(74) *Attorney, Agent, or Firm* — Fenwick & West LLP

(57) ABSTRACT

The present invention is based on the in vivo demonstration that RSV and PIV can be inhibited through intranasal administration of RNAi agents as well as by parenteral administration of such agents. Further, it is shown that effective viral reduction can be achieved with more than one virus being treated concurrently. Based on these findings, the present invention provides general and specific compositions and methods that are useful in reducing RSV or PIV mRNA levels, RSV or PIV protein levels and viral titers in a subject, e.g., a mammal, such as a human. These findings can be applied to other respiratory viruses.

23 Claims, 5 Drawing Sheets

(56) References Cited

OTHER PUBLICATIONS

Bass, B., "The Short Answer," Nature, May 24, 2001, pp. 428-429, vol. 411.
Bernhard, W. et al., "Phosphatidylcholine Molecular Species in Lung Surfactant" *American Journal of Respiratory Cell and Molecular Biology* 25:725-731 (2001).
Bitko, V. et al., "Phenotypic silencing of cytoplasmic genes using sequence-specific double-stranded short interfering RNA and its application in the reverse genetics of wild type negative-strand RNA viruses" *BMC Microbiology* 1:34 (2001).
Bridge, A.J., et al., "Induction of an interferon response by RNAi vectors in mammalian cells" *Nature Genetics* 34:263-264 (2003).
Burke, E. et al., "Profilin Is Required for Optimal Actin-Dependent Transcription of Respiratory Syncytial Virus Genome RNA" *Journal of Virology* 74:669-675 (2000).
Burke, E. et al., "Role of Cellular Actin in the Gene Expressions and Morphogenesis of Human Respiratory Syncytial Virus" *Virology* 252:137-148 (1998).
Caplen, "RNAi as a gene therapy approach" Expert Opin. Biol. Ther. 3(4):575-586 (2003).
Check, "RNA to the rescue?" Nature, 2003, vol. 425, pp. 10-12.
Chi, J.-T., et al., "Genomewide view of gene silencing by small interfering RNAs," PNAS, May 27, 2003, pp. 6343-6346, vol. 100, No. 11.
Coiras, M.T. et al., "Simultaneous Detection of Fourteen Respiratory Viruses in Clinical Specimens by Two Multiplex Reverse Transcription Nested-PCR Assays" *Journal of Medical Virology* 72:484-495 (2004).
Crook, In Basic Principles of Antisense Therapeutics, Springer-Verlag, Eds., New York, 1998, pp. 1-50.
Das, "Human Immunodeficiency Virus Type 1 Escapes from RNA Interference-Mediated Inhibition" *Journal of Virology* 78:2601-2605 (2004).
Definitions of "Invasive" The Free Dictionary by Farlex, [online] [Retrieved on Aug. 6, 2008] Retrieved from the internet <URL:http://www/thefreedictionary.com/invasive>.
Durbin, A.P. et al., "African green monkeys provide a useful nonhuman primate model for the study of human parainfluenza virus types -1, -2, and -3 infection" *Vaccine* 18:2462-2469 (2000).
Durbin, J.E. et al., "The Role of IFN in Respiratory Syncytial Virus Pathogenesis" *Journal of Immunology* 168:2944-2952 (2002).
Easton, A.J. et al., "Animal Pneumoviruses: Molecular Genetics and Pathogenesis" *Clinical Microbiology Reviews* 17:390-412 (2004).
Elbashir, S. et al., "Functional anatomy of siRNAs for mediating efficient RNAi in *Drosophila melanogaster* embryo lysate," The EMBO Journal, 2001, pp. 6877-6888, vol. 20, No. 23.
Elbashir et al., "RNA interference is mediated by 21- and 22-nucleotide RNAs" *Genes and Development* 15:188-200 (2001).
Elbashir, S., et al., "Duplexes of 21-nucleotide RNAs mediate RNA interference in mammalian cell culture," Nature, May 24, 2001, p. 494-498, vol. 411.
Fire, A., et al., "Potent and Specific Genetic Interference by Double Stranded RNA in *Caenorhabditis elegans*," Nature, Feb. 19, 1998, pp. 806-811, vol. 391.
Freymouth et al., "Detection of Respiratory Syncytial Virus, Parainfluenza 3, Adenovirus and Rhinovirus Sequences in Respiratory Tract of Infants by Polymerase Chain Reaction and Hybridization," Clin. Diag. Virol., 1997, 8:31-40.
Ge et al., "Inhibition of influenza virus production in virus-infected mice by RNA interference" *Proceedings of the National Academy of Sciences of the United States of America* 101:8676-8681 (2004).
GenBank Accession No. M22644 (Aug. 3, 1993).
GenBank Accession No. NC_001796 (Dec. 29, 2003).
GenBank Accession U51116, (Mar. 6, 1997).
GenBank Accession No. X65324 (Jan. 9, 2003).
GenBank Accession No. Z11575 (Nov. 23, 1999).
Gilmore, I. et al., "The Design and Exogenous Delivery of siRNA for Post-transcriptional Gene Silencing," The Journal of Drug Targeting, Jul. 2004, pp. 315-340, vol. 12, No. 6.
Graham, B.S. et al., "Primary Respiratory Syncytial Virus Infection in Mice" *Journal of Medical Virology* 26:153-162 (1988).
Gupta, S. et al., "Involvement of Actin Microfilaments in the Replication of Human Parainfluenza Virus Type 3" *Journal of Virology* 72:2655-2662 (1998).
Haeberle, H.A. et al., "Inductible Expression of Inflammatory Chemokines in Respiratory Syncytial Virus-Infected Mice: Role of MIP-1α in Lung Pathology" *Journal of Virology* 75:878-890 (2001).
Haynes, L.M. et al. "Enhanced Disease and Pulmonary Eosinophilia Associated with Formalin-Inactivated Respiratory Syncytial Virus Vaccination Are Linked to G Glycoprotein CX3C-CX3CR1 Interaction and Expression of Substance P" *Journal of Virology* 77:9831-9844 (2003).
Hutvagner, G. et al., "Sequence-Specific Inhibition of Small RNA Function" *PLoS Biology* 2:E98 (2004).
Intellectual Property Office of New Zealand Examination Report, New Zealand Patent Application No. 554494, Jul. 30, 2008 2 pages.
Intellectual Property Office of New Zealand Examination Report, New Zealand Patent Application No. 554494, Nov. 16, 2009, 1 page.
Jackson, A.L. et al., "Expression profiling reveals off-target gene regulation by RNAi" *Nature Biotechnology* 21:635-637 (2003).
Kim, D.H. et al., "Interferon induction by siRNA's and ssRNA's synthesized by phage polymerase" *Nature Biotechnology* 22:321-325 (2004).
Leamond et al., "Targeted Therapy of Respiratory Syncytial Virus in African Green Monkeys by Intranasally Administered 2-5A Antisense," Virology, 2002, pp. 70-77, vol. 292.
Limbach et al., "Summary: the modified nucleosides of RNA" *Nucleic Acids Research* 22:2183-2196 (1994).
Maggon et al., "New drugs and treatment for respiratory syncytial virus" *Reviews in Medical Virology* 14:149-168, 2004.
Mizuta, et al., (Biochem. Biophys. Res. Comm. 279: 158-161 (2000).
Morton, C.J. et al., "Structural characterization of respiratory syncytial virus fusion inhibitor escape mutants: homology model of the F protein and a syncytium formation assay" *Virology* 311:275-288 (2003).
Nykänen et al., "ATP requirements and small interfering RNA structure in the RNA interference pathway" *Cell* 107:309-321 (2001).
Openshaw, P.J.M., "Potential therapeutic implications of new insights into respiratory syncytial virus disease" *Respiratory Research* 3 (suppl 1):S15-S20 (2002).
PCT International Search Report and Written Opinion, International Patent Application No. PCT/US05/38269, Jan. 31, 2007.
Peebles, R.S., Jr. et al., "The Complex Relationship between Respiratory Syncytial Virus and Allergy in Lung Disease" *Viral Immunology* 16:25-34 (2003).
Persengiev, S.P. et al., "Nonspecific, concentration-dependent stimulation and repression of mammalian gene expression by small interfering RNAs (siRNAs)" *RNA* 10:12-18 (2004).
Polack, F.P. et al., "A Role for Immune Complexes in Enhanced Respiratory Syncytial Virus Disease" *The Journal of Experimental Medicine* 196:859-865 (2002).
Ramaswamy, M. et al., "Specific Inhibition of Type I Interferon Signal Transduction by Respiratory Syncytial Virus" *American Journal of Respiratory Cell and Molecular Biology* 30:893-900 (2004).
Razinkov, V. et al., "RSV entry inhibitors block F-protein mediated fusion with model membranes" *Antiviral Research* 55:189-200 (2002).
Reinhart, B.J. et al., "MicroRNAs in plants" *Genes & Development* 16:1616-1626 (2002).
Schlender, J. et al., "Bovine Respiratory Syncytial Virus Nonstructural Proteins NS1 and NS2 Cooperatively Antagonize Alpha/Beta Interferon-Induced Antiviral Response" Journal of Virology 74:8234-8242 (2000).
Russian Office Action, Russian Federation Patent Application No. 2007/115,097, Oct. 20, 2009, 5 pages.
Russian Office Action, Russian Federation Patent Application No. 2007/115,097, Dec. 18, 2009, 4 pages.
Schmidt, A.C. et al., "Recombinant Bovine/Human Parainfluenza Virus Type 3 (B/HPIV3) Expressing the Respiratory Syncytial Virus (RSV) G and F Proteins Can be Used to Achieve Simultaneous Mucosal Immunization against RSV and HPIV3" Journal of Virology 75:4594-4603 (2001).

(56) References Cited

OTHER PUBLICATIONS

Semizarov, D., et al., "Specificity of short interfering RNA determined through gene expression signatures," PNAS, May 27, 2003, pp. 6347-6352, vol. 100, No. 11.
Sledz, C.A. et al., "Activation of the interferon system by short-interfering RNAs" *Nature Cell Biology* 5:834-839 (2003).
State Intellectual Property Office of the People's Republic of China, First Office Action, People's Republic of China Patent Application No. 2005/80044486.8, Jun. 5, 2009, 6 pages.
Sullender, W.M., "Respiratory Syncytial Virus Genetic and Antigenic Diversity" *Clinical Microbiology Reviews* 13:1-15 (2000).
Tompkins, S.M. et al., "Protection against lethal influenza virus challenge by RNA interference in vivo" *Proceedings of the National Academy of Sciences of the United States of America* 101:8682-8686 (2004).
Ueba, O., "Respiratory Syncytial Virus I. Concentration and Purification of the Infectious Virus" *Acta Medica Okayama* 32:265-272 (1978).
United States Patent and Trademark Office Final Office Action, U.S. Appl. No. 11/151,976, Feb. 27, 2009.
Van Shaick, S.M. et al., "Respiratory Syncytial Virus Affects Pulmonary Function of BALB/c Mice" *The Journal of Infectious Diseases* 177:269-276 (1998).
Volovitz, B. et al., "The Release of Leukotrienes in the Respiratory Tract during Infection with Respiratory Syncytial Virus: Role in Obstructive Airway Disease" *Pediatric Research* 24:504-507 (1988).
Welliver, R.C. et al., "Zileuton Reduces Respiratory Illness and Lung Inflammation, during Respiratory Syncytial Virus Infection, in Mice" *Journal of Infectious Diseases* 187:1773-1779 (2003).
Agrawal, S., et al., "Antisense oligonucleotides: towards clinical trials." Trends in Biotechnology. Oct. 1996, vol. 14, pp. 376-387.
Elbashir, S., et al., "Analysis of gene function in somatic mammalian cells using small interfering RNAs," Methods, 2002, pp. 199-213, vol. 26.
Fire, A., "RNA-triggered Gene Silencing," Trends in Genetics, Sep. 1999, pp. 358-363, vol. 15, No. 9.

Tuschl, T., "Functional genomics: RNA sets the standard," Nature, Jan. 16, 2003, vol. 421, No. 6920, pp. 220-221.
Tuschl T., "RNA Interference and Small Interfering RNAs" Chembiochem, 2001, pp. 239-245, vol. 2.
Tuschl, T., et al., "Small Interfering RNAs: A Revolutionary Tool for the Analysis of Gene Function and Gene Therapy," Molecular Interventions, 2002, pp. 158-167, vol. 2, No. 3.
Tuschl, T., "Mammalian RNA Interference," RNAi, A Guide to Gene Silencing, Chapter 13, G.J. Hannon (ed,), 2003, pp. 265-295.
Tuschl, T., et al., "Targeted mRNA Degradation by Double-Stranded RNA in Vitro," Genes & Development, 1999, pp. 3191-3197, vol. 13.
Tuschl, T., "Expanding small RNA interference," Nature Biotechnology, May 2002, pp. 446-448, vol. 20.
Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Examiner's First Report on Australia Patent Application No. 2005314617, May 5, 2010, 2 pages.
Supplementary European Search Report for European Patent Application No. EP 05815963, May 7, 2010, 7 pages.
Barik, S. et al., "Development of Gene-Specific Double-Stranded RNA Drugs," Annals of Medicine, Jan. 1, 2004, pp. 540-551, vol. 36, No. 7.
Bitko V. et al., "Inhibition of respiratory viruses by nasally administered siRNA" Nature Medicine, Jan. 1, 2005, pp. 50-55, vol. 1, No. 1.
Falsey, A.R. et al., "Respiratory Syncytial Virus Infection in Adults" Clinical Microbiological Reviews 13:371-384 (2000).
Office Action for Russian Patent Application No. RU 2010139908/10, Nov. 23, 2012, 6 Pages.
Canadian Intellectual Property Office, Requisition by the Examiner, Canadian Patent Application No. 2,584,309, Jul. 11, 2012, 3 pages.
Massaro, D., et al., "Noninvasive delivery of small inhibitory RNA and other reagents to pulmonary alveoli in mice," *Am J Physiol Lung Cell Mol Physiol* 287:L1066-L1070, 2004.
Decision on Grant of Patent for Invention for Russian Patent Application No. RU 2010139908/10, Apr. 29, 2013, 14 pages.

* cited by examiner

SEQUENCE LISTING

```
<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggtcatcaca cgaatgtaca ac                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttggaacat ctgcagattg tc                                              22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 3
cgauaauaua acugcaagat t                                               21

<210> SEQ ID NO 4
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 4
ucuugcaguu auauuaucgt t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 5
cccuacacca agugauaaut t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 6
auuaucacuu gguguagggt t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 7
gaugccauga uugguuuaat t                                              21

<210> SEQ ID NO 8
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 8
uuaaaccaau cauggcauct t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 9
cgaguuguau guguagcaat t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 10
uugcuacaca uacaacucgt t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 11
gauagacuuc cuagcaggat t                                              21

<210> SEQ ID NO 12
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 12
uccugcuagg aagucuauct t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 13
cguacgcgga auacuucgat t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 14
ucgaaguauu ccgcguacgt t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 15
uucuccgaac gugucacgut t                                              21

<210> SEQ ID NO 16
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: deoxythymidine

<400> SEQUENCE: 16
acgugacacg uucggagaat t                                            21
```

RNAI MODULATION OF RSV, PIV AND OTHER RESPIRATORY VIRUSES AND USES THEREOF

RELATED APPLICATIONS

This application is a divisional application of co-pending U.S. application Ser. No. 12/492,036, filed Jun. 25, 2009, which is a divisional application of U.S. patent application Ser. No. 11/151,976, filed Jun. 14, 2005, now abandoned, which claims the benefit of U.S. Provisional Application No. 60/621,552, filed Oct. 22, 2004. Each of the above-mentioned applications is incorporated herein by reference in its entirety.

REFERENCE TO A SEQUENCE LISTING

This application includes a Sequence Listing submitted electronically as a text file named 17114US_sequencelisting.txt, created on Oct. 6, 2010, with a size of 8.19 kb. The sequence listing is incorporated by reference.

TECHNICAL FIELD

The invention relates to the field of respiratory viral therapy and compositions and methods for modulating viral replication, and more particularly to the down-regulation of a gene(s) of a respiratory virus by oligonucleotides via RNA interference which are administered locally to the lungs and nasal passage via inhalation/intranasally or systemically via injection/intravenous.

BACKGROUND

By virtue of its natural function the respiratory tract is exposed to a slew of airborne pathogens that cause a variety of respiratory ailments. Viral infection of the respiratory tract is the most common cause of infantile hospitalization in the developed world with an estimated 91,000 annual admissions in the US at a cost of $300 M. Human respiratory syncytial virus (RSV) and parainfluenza virus (PIV) are two major agents of respiratory illness; together, they infect the upper and lower respiratory tracts, leading to croup, pneumonia and bronchiolitis (Openshaw, P. J. M. Respir. Res. 3 (Suppl 1), S15-S20 (2002), Easton, A. J., et al., Clin. Microbiol. Rev. 17, 390-412 (2004)). RSV alone infects up to 65% of all babies within the first year of life, and essentially all within the first 2 years. It is a significant cause of morbidity and mortality in the elderly as well. Immunity after RSV infection is neither complete nor lasting, and therefore, repeated infections occur in all age groups. Infants experiencing RSV bronchiolitis are more likely to develop wheezing and asthma later in life. Research for effective treatment and vaccine against RSV has been ongoing for nearly four decades with few successes (Openshaw, P. J. M. Respir. Res. 3 (Suppl 1), S15-S20 (2002), Maggon, K. et al, Rev. Med. Virol. 14, 149-168 (2004)). Currently, no vaccine is clinically approved for either RSV or PIV. Strains of both viruses also exist for nonhuman animals such as the cattle, goat, pig and sheep, causing loss to agriculture and the dairy and meat industry (Easton, A. J., et al., Clin. Microbiol. Rev. 17, 390-412 (2004)).

Both RSV and PIV contain nonsegmented negative-strand RNA genomes and belong to the Paramyxoviridae family. A number of features of these viruses have contributed to the difficulties of prevention and therapy. The viral genomes mutate at a high rate due to the lack of a replicational proofreading mechanism of the RNA genomes, presenting a significant challenge in designing a reliable vaccine or antiviral (Sullender, W. M. Clin. Microbiol. Rev. 13, 1-15 (2000)). Promising inhibitors of the RSV fusion protein (F) were abandoned partly because the virus developed resistant mutations that were mapped to the F gene (Razinkov, V., et. al., Antivir. Res. 55, 189-200 (2002), Morton, C. J. et al. Virology 311, 275-288 (2003)). Both viruses associate with cellular proteins, adding to the difficulty of obtaining cell-free viral material for vaccination (Burke, E., et al., Virology 252, 137-148 (1998), Burke, E., et al., J. Virol. 74, 669-675 (2000), Gupta, S., et al., J. Virol. 72, 2655-2662 (1998)). Finally, the immunology of both, and especially that of RSV, is exquisitely complex (Peebles, R. S., Jr., et al., Viral. Immunol. 16, 25-34 (2003), Haynes, L. M., et al., J. Virol. 77, 9831-9844 (2003)). Use of denatured RSV proteins as vaccines leads to "immunopotentiation" or vaccine-enhanced disease (Polack, F. P. et al. J. Exp. Med. 196, 859-865 (2002)), and this phenomenon has been neither tested nor ruled out for PIV. The overall problem is underscored by the recent closure of a number of anti-RSV biopharma programs.

The RSV genome comprises a single strand of negative sense RNA that is 15,222 nucleotides in length and yields eleven major proteins. (Falsey, A. R., and E. E. Walsh, 2000, Clinical Microbiological Reviews 13:371-84.) Two of these proteins, the F (fusion) and G (attachment) glycoproteins, are the major surface proteins and the most important for inducing protective immunity. The SH (small hydrophobic) protein, the M (matrix) protein, and the M2 (22 kDa) protein are associated with the viral envelope but do not induce a protective immune response. The N (major nucleocapsid associated protein), P (phosphoprotein), and L (major polymerase protein) proteins are found associated with virion RNA. The two non-structural proteins, NS1 and NS2, presumably participate in host-virus interaction but are not present in infectious virions.

Human RSV strains have been classified into two major groups, A and B. The G glycoprotein has been shown to be the most divergent among RSV proteins. Variability of the RSV G glycoprotein between and within the two RSV groups is believed to be important to the ability of RSV to cause yearly outbreaks of disease. The G glycoprotein comprises 289-299 amino acids (depending on RSV strain), and has an intracellular, transmembrane, and highly glycosylated stalk structure of 90 kDa, as well as heparin-binding domains. The glycoprotein exists in secreted and membrane-bound forms.

Successful methods of treating RSV infection are currently unavailable (Maggon and Bark 2004, Reviews in Medical Virology 14:149-68). Infection of the lower respiratory tract with RSV is a self-limiting condition in most cases. No definitive guidelines or criteria exist on how to treat or when to admit or discharge infants and children with the disease. Hypoxia, which can occur in association with RSV infection, can be treated with oxygen via a nasal cannula. Mechanical ventilation for children with respiratory failure, shock, or recurrent apnea can lower mortality. Some physicians prescribe steroids. However, several studies have shown that steroid therapy does not affect the clinical course of infants and children admitted to the hospital with bronchiolitis. Thus corticosteroids, alone or in combination with bronchodilators, may be useless in the management of bronchiolitis in otherwise healthy unventilated patients. In infants and children with underlying cardiopulmonary diseases, such as bronchopulmonary dysphasia and asthma, steroids have also been used.

Ribavirin, a guanosine analogue with antiviral activity, has been used to treat infants and children with RSV bronchiolitis since the mid 1980s, but many studies evaluating its use have shown conflicting results. In most centers, the use of ribavirin is now restricted to immunocompromised patients and to those who are severely ill.

The severity of RSV bronchiolitis has been associated with low serum retinol concentrations, but trials in hospitalized children with RSV bronchiolitis have shown that vitamin A supplementation provides no beneficial effect. Therapeutic trials of 1500 mg/kg intravenous RSV immune globulin or 100 mg/kg inhaled immune globulin for RSV lower-respiratory-tract infection have also failed to show substantial beneficial effects.

In developed countries, the treatment of RSV lower-respiratory-tract infection is generally limited to symptomatic therapy. Antiviral therapy is usually limited to life-threatening situations due to its high cost and to the lack of consensus on efficacy. In developing countries, oxygen is the main therapy (when available), and the only way to lower mortality is through prevention.

RNA interference or "RNAi" is a term initially coined by Fire and co-workers to describe the observation that double-stranded RNA (dsRNA) can block gene expression when it is introduced into worms (Fire et al., *Nature* 391:806-811, 1998). Short dsRNA directs gene-specific, post-transcriptional silencing in many organisms, including vertebrates, and has provided a new tool for studying gene function. RNAi has been suggested as a method of developing a new class of therapeutic agents. However, to date, these have remained mostly as suggestions with no demonstrate proof that RNAi can be used therapeutically.

Therefore, there is a need for safe and effective vaccines against RSV, especially for infants and children. There is also a need for therapeutic agents and methods for treating RSV infection at all ages and in immuno-compromised individuals. There is also a need for scientific methods to characterize the protective immune response to RSV so that the pathogenesis of the disease can be studied, and screening for therapeutic agents and vaccines can be facilitated. The present invention overcomes previous shortcomings in the art by providing methods and compositions effective for modulating or preventing RSV and PIV infection, which be expanded to other respiratory viruses. Specifically, the present invention advances the art by providing iRNA agents that have been shown to reduce RSV and PIV levels in vivo and a showing of therapeutic activity of this class of molecules. It is further demonstrated that more than one virus can be treated concurrently.

SUMMARY

The present invention is based on the in vivo demonstration that RSV and PIV can be inhibited through intranasal administration of RNAi agents, as well as by parenteral administration of such agents. Further, it is shown that effective viral titer reduction can be achieved with more than one virus being treated concurrently using two different iRNA agents. Based on these findings, the present invention provides general and specific compositions and methods that are useful in reducing RSV or PIV mRNA levels, RSV or PIV protein levels and RSV and PIV viral titers in a subject, e.g., a mammal, such as a human. These findings can be applied to other respiratory viruses.

The present invention specifically provides iRNA agents consisting of or comprising at least 15 contiguous nucleotides of one of the genes of RSV, PIV or other respiratory virus, particularly the P gene of RSV or PIV and the N G, F, SH, M, and L genes of RSV. The iRNA agent preferably comprises less than 30 nucleotides per strand, e.g., 21-23 nucleotides. The double stranded iRNA agent can either have blunt ends or more preferably have overhangs of 1-4 nucleotides from one or both 3' ends of the agent.

Further, the iRNA agent can either contain only naturally occurring ribonucleotide subunits, or can be synthesized so as to contain one or more modifications to the sugar or base of one or more of the ribonucleotide subunits that is included in the agent. The iRNA agent can be further modified so as to be attached to a ligand that is selected to improve stability, distribution or cellular uptake of the agent, e.g. cholesterol. The iRNA agents can further be in isolated form or can be part of a pharmaceutical composition used for the methods described herein, particularly as a pharmaceutical composition formulated for delivery to the lungs or nasal passage or formulated for parental administration. The pharmaceutical compositions can contain one or more iRNA agents, and in some embodiments, will contain two or more iRNA agents, each one directed to a different respiratory virus, such as RSV and PIV.

The present invention further provides methods for reducing the level of RSV, PIV or other respiratory viral mRNA in a cell. The present methods utilize the cellular mechanisms involved in RNA interference to selectively degrade the viral mRNA in a cell and are comprised of the step of contacting a cell with one of the antiviral iRNA agents of the present invention. Such methods can be preformed directly on a cell or can be performed on a mammalian subject by administering to a subject one of the iRNA agents/pharmaceutical compositions of the present invention. Reduction of viral mRNA in a cells results in a reduction in the amount of viral protein produced, and in an organism, results in a decrease in replicating viral titer. The Examples demonstrate this with PIV and RSV and this can be extended to other respiratory viruses.

The present invention further provides methods for reducing the level of two or more respiratory viral mRNA in a cell, each one coming from a different virus. The present methods utilize the cellular mechanisms involved in RNA interference to selectively degrade the viral mRNA from two different viruses in a cell and are comprised of the step of contacting a cell with two of the antiviral iRNA agents of the present invention. Such methods can be preformed directly on a cell or can be performed on a mammalian subject by administering to a subject two of the iRNA agents of the present invention. Reduction of viral mRNA from two different viruses in a cells results in a reduction in the amount of both viral protein produced, and in an organism, results in a decrease in replicating viral titer of both viruses. The Examples demonstrate this with PIV and RSV and concurrent administration of iRNA agents. This embodiment of the present invention can be applied to any two respiratory viruses.

The methods and compositions of the invention, e.g., the methods and iRNA compositions can be used with any dosage and/or formulation described herein, as well as with any route of administration described herein. Particularly important is the showing herein of intranasal administration of an iRNA agent and its ability to inhibit viral replication in respiratory tissues. This finding can be applied to other respiratory virus, such as PIV as shown in the Examples and to other routes of local delivery to the lungs, e.g. via inhalation/nebulization.

The details of one or more embodiments of the invention are set forth in the accompanying drawings and the description below. Other features, objects, and advantages of the invention will be apparent from this description, the drawings, and from the claims. This application incorporates all cited references, patents, and patent applications by references in their entirety for all purposes.

DETAILED DESCRIPTION

Figure 1:
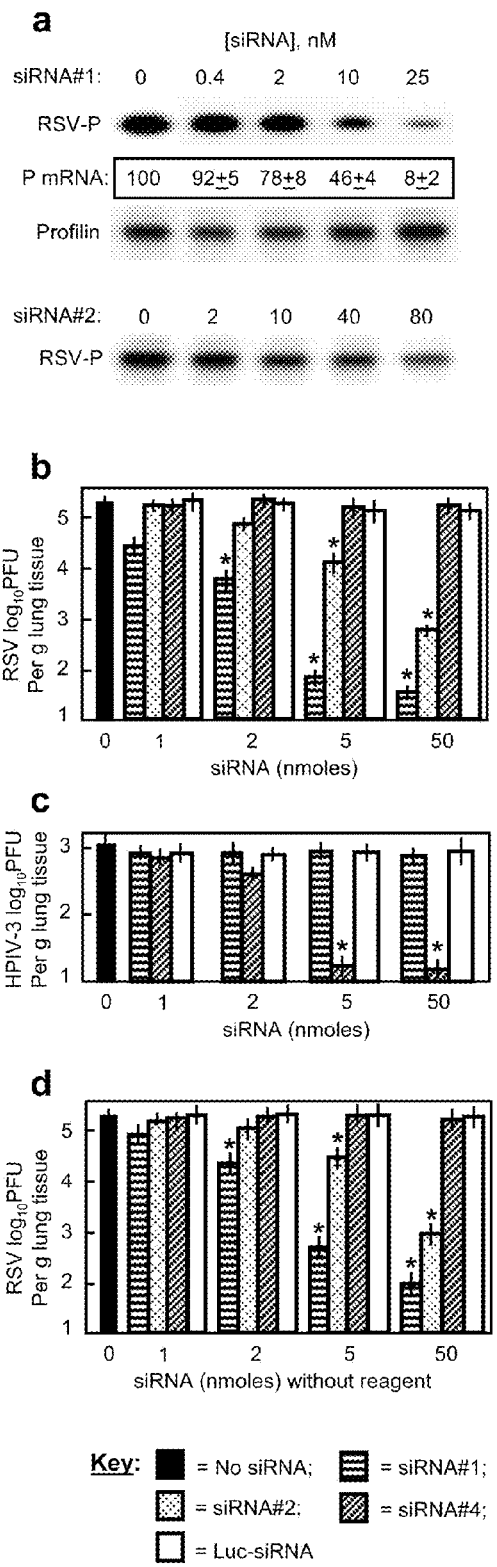
FIG. 1. Titration of anti-viral siRNAs ex vivo. (a) Immunoblot analysis of total proteins of RSV-infected A549 cells (ex vivo) with profilin as the internal control. The numbers in the box represent levels of target P mRNA following siRNA treatment, expressed as percentage of untreated levels. In the following three panels, virus was administered 4 hrs after siRNA. (b) Pulmonary infectious virus in RSV-infected mice (n=8 for each data point). (c) Pulmonary infectious virus in HPIV3-infected mice (n=8 for each data point). (d) As in (b) except that naked siRNA was administered without any transfection reagent. Asterisks indicate significant inhibition (P<0.05). siRNAs are described in Table 1.

For ease of exposition the term "nucleotide" or "ribonucleotide" is sometimes used herein in reference to one or more monomeric subunits of an RNA agent. It will be understood that the usage of the term "ribonucleotide" or "nucleotide" herein can, in the case of a modified RNA or nucleotide surrogate, also refer to a modified nucleotide, or surrogate replacement moiety, as further described below, at one or more positions.

An "RNA agent" as used herein, is an unmodified RNA, modified RNA, or nucleoside surrogates, all of which are described herein or are well known in the RNA synthetic art. While numerous modified RNAs and nucleoside surrogates are described, preferred examples include those which have greater resistance to nuclease degradation than do unmodified RNAs. Preferred examples include those that have a 2' sugar modification, a modification in a single strand overhang, preferably a 3' single strand overhang, or, particularly if single stranded, a 5'-modification which includes one or more phosphate groups or one or more analogs of a phosphate group.

An "iRNA agent" sometimes referred to as an "RNAi agent" (abbreviation for "interfering RNA agent") as used herein, is an RNA agent, which can down-regulate the expression of a target gene, e.g., RSV. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand or can include more than one strands, e.g., it can be a double stranded (ds) iRNA agent. If the iRNA agent is a single strand it is particularly preferred that it include a 5' modification which includes one or more phosphate groups or one or more analogs of a phosphate group.

A "single strand iRNA agent" as used herein, is an iRNA agent which is made up of a single molecule. It may include a duplexed region, formed by intra-strand pairing, e.g., it may be, or include, a hairpin or panhandle structure. Single strand iRNA agents are preferably antisense with regard to the target molecule.

A "ds iRNA agent" (abbreviation for "double stranded iRNA agent"), as used herein, is an iRNA agent which includes more than one, and preferably two, strands in which interchain hybridization can form a region of duplex structure.

The isolated iRNA agents described herein, including ds iRNA agents and siRNA agents, can mediate silencing of a target gene, e.g., by RNA degradation. For convenience, such RNA is also referred to herein as the RNA to be silenced. Such a gene is also referred to as a target gene. Preferably, the RNA to be silenced is a gene product of an endogenous RSV gene.

As used herein, the phrase "mediates RNAi" refers to the ability of an agent to silence, in a sequence specific manner, a target gene. "Silencing a target gene" means the process whereby a cell containing and/or secreting a certain product of the target gene when not in contact with the agent, will contain and/or secret at least 10%, 20%, 30%, 40%, 50%, 60%, 70%, 80%, or 90% less of such gene product when contacted with the agent, as compared to a similar cell which has not been contacted with the agent. Such product of the target gene can, for example, be a messenger RNA (mRNA), a protein, or a regulatory element.

In the anti viral uses of the present invention, silencing of a target gene will result in a reduction in "viral titer" in the cell. As used herein, "reduction in viral titer" refers to a decrease in the number of viable virus produced by a cell or found in an organism undergoing the silencing of a viral target gene. Reduction in the cellular amount of virus produced will preferably lead to a decrease in the amount of measurable virus produced in the tissues of a subject undergoing treatment and a reduction in the severity of the symptoms of the viral infection. iRNA agents of the present invention are also referred to as "antiviral iRNA agents".

As used herein, a "RSV gene" refers to any one of the genes identified in the RSV virus genome (See Falsey, A. R., and E. E. Walsh, 2000, Clinical Microbiological Reviews 13:371-84). These genes are readily known in the art and include the F, G, SH, M, N, P and L genes.

As used herein, a "PIV gene" refers to any one of the genes identified in the PIV virus genome (See GenBank Accession #NC_001796). These genes are readily known in the art and include the N, P, C, D, V, M, F, FIN, and L genes.

As used herein, "respiratory virus" refers to viruses that replicate in cells of the respiratory system. Such viruses include, but are not limited to RSV, PIV, influenza, metapneumovirus, adenovirus, and coronavirus (such as SARS).

As used herein, the term "complementary" is used to indicate a sufficient degree of complementarity such that stable and specific binding occurs between a compound of the invention and a target RNA molecule, e.g. an RSV, PIV or other respiratory viral mRNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 4 nucleotides.

As used herein, an iRNA agent is "sufficiently complementary" to a target RNA, e.g., a target mRNA (e.g., a target RSV or PIV mRNA) if the iRNA agent reduces the production of a protein encoded by the target RNA in a cell. The iRNA agent may also be "exactly complementary" (excluding the SRMS containing subunit(s)) to the target RNA, e.g., the target RNA and the iRNA agent anneal, preferably to form a hybrid made exclusively of Watson-Crick base pairs in the region of exact complementarity. A "sufficiently complementary" iRNA agent can include an internal region (e.g., of at least 10 nucleotides) that is exactly complementary to a target viral RNA. Moreover, in some embodiments, the iRNA agent specifically discriminates a single-nucleotide difference. In this case, the iRNA agent only mediates RNAi if exact complementary is found in the region (e.g., within 7 nucleotides of) the single-nucleotide difference. Preferred iRNA agents will be based on or consist or comprise the sense and antisense sequences provided in the Examples.

As used herein, "essentially identical" when used referring to a first nucleotide sequence in comparison to a second nucleotide sequence means that the first nucleotide sequence is identical to the second nucleotide sequence except for up to one, two or three nucleotide substitutions (e.g. adenosine replaced by uracil).

As used herein, a "subject" refers to a mammalian organism undergoing treatment for a disorder mediated by viral expression, such as RSV or PIV infection or undergoing treatment prophylactically to prevent viral infection. The subject can be any mammal, such as a primate, cow, horse, mouse, rat, dog, pig, goat. In the preferred embodiment, the subject is a human.

As used herein, treating RSV infection, PIV infection, or other respiratory virus infection, refers to the amelioration of any biological or pathological endpoints that 1) is mediated in part by the presence of the virus in the subject and 2) whose outcome can be affected by reducing the level of viral protein present.

As used herein, "co-administration" refers to administering to a subject two or more agents, and in particular two or more iRNA agents. The agents can be contained in a single pharmaceutical composition and be administered at the same time, or the agents can be contained in separate formulation and administered serially to a subject. So long as the two agents can be detected in the subject at the same time, the two agents are said to be co-administered.

Because iRNA agent mediated silencing can persist for several days after administering the iRNA agent composition, in many instances, it is possible to administer the composition with a frequency of less than once per day, or, for some instances, only once for the entire therapeutic regimen.

Design and Selection of iRNA Agents

The present invention is based on the demonstration of target gene silencing of a respiratory viral gene in vivo following local administration to the lungs and nasal passage of an iRNA agent either via intranasal administration/inhalation or systemically/parenterally via injection and the resulting treatment of viral infection. The present invention is further extended to the use of iRNA agents to more than one respiratory virus and the treatment of both virus infections with co-administration of two or more iRNA agents.

Based on these results, the invention specifically provides an iRNA agent that can be used in treating viral infection, particularly respiratory viruses and in particular RSV or PIV infection, in isolated form and as a pharmaceutical composition described below. Such agents will include a sense strand having at least 15 contiguous nucleotides that are complementary to a viral gene and an antisense strand having at least 15 contiguous nucleotides that is complementary to the sense strand sequences. Particularly useful are iRNA agents that comprise a nucleotide sequence from the P protein gene of RSV or PIV. Other target genes in RSV include the F, G, SH, M, N and L. Other genes in PIV include N, P, C, D, V, M, F, FIN, and L genes. Exemplified agents are provided in Table 1.

Candidate iRNA agents can be designed by performing, for example, a gene walk analysis of the viral genes that will serve as the iRNA target. Overlapping, adjacent, or closely spaced candidate agents corresponding to all or some of the transcribed region can be generated and tested. Each of the iRNA agents can be tested and evaluated for the ability to down regulate the target gene expression (see below, "Evaluation of Candidate iRNA agents").

An iRNA agent can be rationally designed based on sequence information and desired characteristics. For example, an iRNA agent can be designed according to the relative melting temperature of the candidate duplex. Generally, the duplex should have a lower melting temperature at the 5' end of the antisense strand than at the 3' end of the antisense strand.

Accordingly, the present invention provides iRNA agents comprising a sense strand and antisense strand each comprising a sequence of at least 15, 16, 17, 18, 19, 20, 21 or 23 nucleotides which is essentially identical to, as defined above, to a portion of a gene from a respiratory virus, particularly the P protein genes of RSV or PIV. Exemplified iRNA agents include those that comprise 15 contiguous nucleotides from one of the agents provided in Table 1.

The antisense strand of an iRNA agent should be equal to or at least, 15, 16 17, 18, 19, 25, 29, 40, or 50 nucleotides in length. It should be equal to or less than 50, 40, or 30, nucleotides in length. Preferred ranges are 15-30, 17 to 25, 19 to 23, and 19 to 21 nucleotides in length. In several embodiments, the agent will comprise 15 nucleotides from one of the agents in Table 1.

The sense strand of an iRNA agent should be equal to or at least 15, 16 17, 18, 19, 25, 29, 40, or 50 nucleotides in length. It should be equal to or less than 50, 40, or 30 nucleotides in length. Preferred ranges are 15-30, 17 to 25, 19 to 23, and 19 to 21 nucleotides in length. In several embodiments, the agent will comprise 15 nucleotides from one of the agents in Table 1.

The double stranded portion of an iRNA agent should be equal to or at least, 15, 16 17, 18, 19, 20, 21, 22, 23, 24, 25, 29, 40, or 50 nucleotide pairs in length. It should be equal to or less than 50, 40, or 30 nucleotides pairs in length. Preferred ranges are 15-30, 17 to 25, 19 to 23, and 19 to 21 nucleotides pairs in length.

The agents provided in Table 1 are 21 nucleotide in length for each strand. The iRNA agents contain a 19 nucleotide double stranded region with a 2 nucleotide overhang on each of the 3' ends of the agent. These agents can be modified as described herein to obtain equivalent agents comprising at least a portion of these sequences and or modifications to the oligonucleotide bases and linkages.

Generally, the iRNA agents of the instant invention include a region of sufficient complementarity to the viral gene, e.g. the P protein of RSV or PIV, and are of sufficient length in terms of nucleotides, that the iRNA agent, or a fragment thereof, can mediate down regulation of the specific viral gene. The antisense strands of the iRNA agents of the present invention are preferably fully complementary to the mRNA sequences of viral gene, as is herein for the P proteins of RSV and PIV. However, it is not necessary that there be perfect complementarity between the iRNA agent and the target, but the correspondence must be sufficient to enable the iRNA agent, or a cleavage product thereof, to direct sequence specific silencing, e.g., by RNAi cleavage of an RSV mRNA.

Therefore, the iRNA agents of the instant invention include agents comprising a sense strand and antisense strand each comprising a sequence of at least 16, 17 or 18 nucleotides which is essentially identical, as defined below, to one of the sequences of a viral gene, particularly the P protein of RSV or PIV, except that not more than 1, 2 or 3 nucleotides per strand, respectively, have been substituted by other nucleotides (e.g. adenosine replaced by uracil), while essentially retaining the ability to inhibit RSV expression in cultured human cells, as defined below. These agents will therefore possess at least 15 nucleotides identical to one of the sequences of a viral gene, particularly the P protein gene of RSV or PIV, but 1, 2 or 3 base mismatches with respect to either the target viral mRNA sequence or between the sense and antisense strand are introduced. Mismatches to the target viral mRNA sequence, particularly in the antisense strand, are most tolerated in the terminal regions and if present are preferably in a terminal region or regions, e.g., within 6, 5, 4, or 3 nucleotides of a 5' and/or 3' terminus, most preferably within 6, 5, 4, or 3 nucleotides of the 5'-terminus of the sense strand or the 3'-terminus of the antisense strand. The sense strand need only be sufficiently complementary with the antisense strand to maintain the overall double stranded character of the molecule.

It is preferred that the sense and antisense strands be chosen such that the iRNA agent includes a single strand or unpaired region at one or both ends of the molecule, such as those exemplified in Table 1. Thus, an iRNA agent contains sense and antisense strands, preferably paired to contain an overhang, e.g., one or two 5' or 3' overhangs but preferably a 3' overhang of 2-3 nucleotides. Most embodiments will have a 3' overhang. Preferred siRNA agents will have single-stranded overhangs, preferably 3' overhangs, of 1 to 4, or preferably 2 or 3 nucleotides, in length one or both ends of the iRNA agent. The overhangs can be the result of one strand being longer than the other, or the result of two strands of the same length being staggered. 5'-ends are preferably phosphorylated.

Preferred lengths for the duplexed region is between 15 and 30, most preferably 18, 19, 20, 21, 22, and 23 nucleotides in length, e.g., in the siRNA agent range discussed above. Embodiments in which the two strands of the siRNA agent are linked, e.g., covalently linked are also included. Hairpin, or other single strand structures which provide the required double stranded region, and preferably a 3' overhang are also within the invention.

Evaluation of Candidate iRNA Agents

A candidate iRNA agent can be evaluated for its ability to down regulate target gene expression. For example, a candidate iRNA agent can be provided, and contacted with a cell, e.g. a human cell, that has been infected with or will be infected with the virus of interest, e.g., a virus containing the target gene. Alternatively, the cell can transfected with a construct from which target viral gene is expressed, thus preventing the need for a viral infectivity model. The level of target gene expression prior to and following contact with the candidate iRNA agent can be compared, e.g. on an mRNA, protein level or viral titer. If it is determined that the amount of RNA, protein or virus expressed from the target gene is lower following contact with the iRNA agent, then it can be concluded that the iRNA agent down regulates target gene expression. The level of target viral RNA or viral protein in the cell or viral titer in a cell or tissue can be determined by any method desired. For example, the level of target RNA can be determined by Northern blot analysis, reverse transcription coupled with polymerase chain reaction (RT-PCR), bDNA analysis, or RNAse protection assay. The level of protein can be determined, for example, by Western blot analysis or immuno-flouresence. Viral titer can be detected through a plaque formation assay.

Stability Testing, Modification, and Retesting of iRNA Agents

A candidate iRNA agent can be evaluated with respect to stability, e.g., its susceptibility to cleavage by an endonuclease or exonuclease, such as when the iRNA agent is introduced into the body of a subject. Methods can be employed to identify sites that are susceptible to modification, particularly cleavage, e.g., cleavage by a component found in the body of a subject.

When sites susceptible to cleavage are identified, a further iRNA agent can be designed and/or synthesized wherein the potential cleavage site is made resistant to cleavage, e.g. by introduction of a 2'-modification on the site of cleavage, e.g. a 2'-O-mathyl group. This further iRNA agent can be retested for stability, and this process may be iterated until an iRNA agent is found exhibiting the desired stability.

In Vivo Testing

An iRNA agent identified as being capable of inhibiting RSV gene expression can be tested for functionality in vivo in an animal model (e.g., in a mammal, such as in mouse or rat) as shown in the examples. For example, the iRNA agent can be administered to an animal, and the iRNA agent evaluated with respect to its biodistribution, stability, and its ability to inhibit viral, e.g. RSV or PIV, gene expression or reduce viral titer.

The iRNA agent can be administered directly to the target tissue, such as by injection, or the iRNA agent can be administered to the animal model in the same manner that it would be administered to a human. As shown herein, the agent can be preferably administered via inhalation as a means of treating viral infection.

The iRNA agent can also be evaluated for its intracellular distribution. The evaluation can include determining whether the iRNA agent was taken up into the cell. The evaluation can also include determining the stability (e.g., the half-life) of the iRNA agent. Evaluation of an iRNA agent in vivo can be facilitated by use of an iRNA agent conjugated to a traceable marker (e.g., a fluorescent marker such as fluorescein; a radioactive label, such as $^{35}$S, $^{32}$P, $^{33}$P, or $^{3}$H; gold particles; or antigen particles for immunohistochemistry).

An iRNA agent useful for monitoring biodistribution can lack gene silencing activity in vivo. For example, the iRNA agent can target a gene not present in the animal (e.g., an iRNA agent injected into mouse can target luciferase), or an iRNA agent can have a non-sense sequence, which does not target any gene, e.g., any endogenous gene). Localization/biodistribution of the iRNA can be monitored, e.g. by a traceable label attached to the iRNA agent, such as a traceable agent described above The iRNA agent can be evaluated with respect to its ability to down regulate viral gene expression. Levels of viral gene expression in vivo can be measured, for example, by in situ hybridization, or by the isolation of RNA from tissue prior to and following exposure to the iRNA agent. Where the animal needs to be sacrificed in order to harvest the tissue, an untreated control animal will serve for comparison. Target viral mRNA can be detected by any desired method, including but not limited to RT-PCR, Northern blot, branched-DNA assay, or RNAase protection assay. Alternatively, or additionally, viral gene expression can be monitored by performing Western blot analysis on tissue extracts treated with the iRNA agent. Viral titer can be determined using a pfu assy.

iRNA Chemistry

Described herein are isolated iRNA agents, e.g., RNA molecules, (double-stranded; single-stranded) that mediate RNAi to inhibit expression of a viral gene, e.g. the P protein of RSV or PIV.

RNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) *Nucleic Acids Res.* 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of each of the above are discussed herein.

Modifications described herein can be incorporated into any double-stranded RNA and RNA-like molecule described herein, e.g., an iRNA agent. It may be desirable to modify one or both of the antisense and sense strands of an iRNA agent. As nucleic acids are polymers of subunits or monomers, many of the modifications described below occur at a position which is repeated within a nucleic acid, e.g., a modification of a base, or a phosphate moiety, or the non-linking O of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g. pharmacodynamic properties, which are further discussed below. Other suitable modifications to a sugar, base, or backbone of an iRNA agent are described in co-owned PCT Application No. PCT/US2004/01193, filed Jan. 16, 2004. An iRNA agent can include a non-naturally occurring base, such as the bases described in co-owned PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in co-owned PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in co-owned PCT Application No. PCT/US2004/07070 filed on Mar. 8, 2004.

An iRNA agent can include ligand-conjugated monomer subunits and monomers for oligonucleotide synthesis. Exemplary monomers are described in co-owned U.S. application Ser. No. 10/916,185, filed on Aug. 10, 2004.

An iRNA agent can have a ZXY structure, such as is described in co-owned PCT Application No. PCT/US2004/07070 filed on Mar. 8, 2004.

An iRNA agent can be complexed with an amphipathic moiety. Exemplary amphipathic moieties for use with iRNA agents are described in co-owned PCT Application No. PCT/US2004/07070 filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in co-owned PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in co-owned PCT Application No. PCT/US2004/07070 filed on Mar. 8, 2004.

Enhanced Nuclease Resistance

An iRNA agent, e.g., an iRNA agent that targets RSV can have enhanced resistance to nucleases. One way to increase resistance is to identify cleavage sites and modify such sites to inhibit cleavage. For example, the dinucleotides 5'-UA-3', 5'-UG-3', 5'-CA-3', 5'-UU-3', or 5'-CC-3' can serve as cleavage sites.

For increased nuclease resistance and/or binding affinity to the target, an iRNA agent, e.g., the sense and/or antisense strands of the iRNA agent, can include, for example, 2'-modified ribose units and/or phosphorothioate linkages. E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH3, 2'-O-allyl, 2'-C-allyl, and 2'-fluoro.

To maximize nuclease resistance, the 2' modifications can be used in combination with one or more phosphate linker modifications (e.g., phosphorothioate). The so-called "chimeric" oligonucleotides are those that contain two or more different modifications.

In certain embodiments, all the pyrimidines of an iRNA agent carry a 2'-modification, and the iRNA agent therefore has enhanced resistance to endonucleases. Enhanced nuclease resistance can also be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleo wherein the 5'-cytidine is a 2'-modified nucleotide. The iRNA agent can include at least 2, at least 3, at least 4 or at least 5 of such dinucleotides.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In a preferred embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In preferred embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

Thus, an iRNA agent can include monomers which have been modified so as to inhibit degradation, e.g., by nucleases, e.g., endonucleases or exonucleases, found in the body of a subject. These monomers are referred to herein as NRMs, or Nuclease Resistance promoting Monomers or modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

Modifications that can be useful for producing iRNA agents that meet the preferred nuclease resistance criteria delineated above can include one or more of the following chemical and/or stereochemical modifications of the sugar, base, and/or phosphate backbone:

(i) chiral ($S_p$) thioates. Thus, preferred NRMs include nucleotide dimers with an enriched or pure for a particular chiral form of a modified phosphate group containing a heteroatom at the nonbridging position, e.g., Sp or Rp, at the position X, where this is the position normally occupied by the oxygen. The atom at X can also be S, Se, $Nr_2$, or $Br_3$. When X is S, enriched or chirally pure Sp linkage is preferred. Enriched means at least 70, 80, 90, 95, or 99% of the preferred form. Such NRMs are discussed in more detail below;

(ii) attachment of one or more cationic groups to the sugar, base, and/or the phosphorus atom of a phosphate or modified phosphate backbone moiety. Thus, preferred NRMs include monomers at the terminal position derivatized at a cationic group. As the 5'-end of an antisense sequence should have a terminal —OH or phosphate group this NRM is preferably not used at the 5'-end of an anti-sense sequence. The group should be attached at a position on the base which minimizes interference with H bond formation and hybridization, e.g., away form the face which interacts with the complementary base on the other strand, e.g, at the 5' position of a pyrimidine or a 7-position of a purine. These are discussed in more detail below;

(iii) nonphosphate linkages at the termini. Thus, preferred NRMs include Non-phosphate linkages, e.g., a linkage of 4 atoms which confers greater resistance to cleavage than does a phosphate bond. Examples include 3' $CH2-NCH_3$—O—$CH_2$-5' and 3' $CH_2$—NH—(O=)—$CH_2$-5';

(iv) 3'-bridging thiophosphates and 5'-bridging thiophosphates. Thus, preferred NRM's can included these structures;

(v) L-RNA, 2'-5' linkages, inverted linkages, a-nucleosides. Thus, other preferred NRM's include: L nucleosides and dimeric nucleotides derived from L-nucleosides; 2'-5' phosphate, non-phosphate and modified phosphate linkages (e.g., thiophosphates, phosphoramidates and boronophosphates); dimers having inverted linkages, e.g., 3'-3' or 5'-5' linkages; monomers having an alpha linkage at the 1' site on the sugar, e.g., the structures described herein having an alpha linkage;

(vi) conjugate groups. Thus, preferred NRM's can include, e.g., a targeting moiety or a conjugated ligand described herein conjugated with the monomer, e.g., through the sugar, base, or backbone;

(vi) abasic linkages. Thus, preferred NRM's can include an abasic monomer, e.g., an abasic monomer as described herein (e.g., a nucleobaseless monomer); an aromatic or heterocyclic or polyheterocyclic aromatic monomer as described herein; and (vii) 5'-phosphonates and 5'-phosphate prodrugs. Thus, preferred NRM's include monomers, preferably at the terminal position, e.g., the 5' position, in which one or more atoms of the phosphate group is derivatized with a protecting group, which protecting group or groups, are removed as a result of the action of a component in the subject's body, e.g, a carboxyesterase or an enzyme present in the subject's body. E.g., a phosphate prodrug in which a carboxy esterase cleaves the protected molecule resulting in the production of a thioate anion which attacks a carbon adjacent to the O of a phosphate and resulting in the production of an unprotected phosphate.

One or more different NRM modifications can be introduced into an iRNA agent or into a sequence of an iRNA agent. An NRM modification can be used more than once in a sequence or in an iRNA agent. As some NRMs interfere with hybridization, the total number incorporated should be such that acceptable levels of iRNA agent duplex formation are maintained.

In some embodiments NRM modifications are introduced into the terminal cleavage site or in the cleavage region of a sequence (a sense strand or sequence) which does not target a desired sequence or gene in the subject. This can reduce off-target silencing.

Nuclease resistant modifications include some which can be placed only at the terminus and others which can go at any position. Generally, modifications that can inhibit hybridization are used only in terminal regions, and preferably not at the cleavage site or in the cleavage region of a sequence which targets a subject sequence or gene. They can be used anywhere in a sense sequence, provided that sufficient hybridization between the two sequences of the iRNA agent is maintained. In some embodiments it is desirable to put the NRM at the cleavage site or in the cleavage region of a sequence which does not target a subject sequence or gene, as it can minimize off-target silencing.

In most cases, the nuclease-resistance promoting modifications will be distributed differently depending on whether the sequence will target a sequence in the subject (often referred to as an anti-sense sequence) or will not target a sequence in the subject (often referred to as a sense sequence). If a sequence is to target a sequence in the subject, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nt guide RNA, or about 10 or 11 nucleotides upstream of the first nucleotide which is complementary to the guide sequence. As used herein cleavage site refers to the nucleotide on either side of the cleavage site, on the target or on the iRNA agent strand which hybridizes to it. Cleavage region means a nucleotide with 1, 2, or 3 nucleotides of the cleave site, in either direction.)

Such modifications can be introduced into the terminal regions, e.g., at the terminal position or with 2, 3, 4, or 5 positions of the terminus, of a sequence which targets or a sequence which does not target a sequence in the subject.

Tethered Ligands

The properties of an iRNA agent, including its pharmacological properties, can be influenced and tailored, for example, by the introduction of ligands, e.g. tethered ligands.

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. The ligand or tethered ligand may be present on the ligand-conjugated monomer\when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-$(CH_2)_n NH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics.

Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a liver cell or a cell of the jejunum. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

5'-Phosphate Modifications

In preferred embodiments, iRNA agents are 5' phosphorylated or include a phosphoryl analog at the 5' prime terminus. 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-).

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Delivery of iRNA Agents to Tissues and Cells

Formulation

The iRNA agents described herein can be formulated for administration to a subject, preferably for administration locally to the lungs and nasal passage (respiratory tissues) via inhalation or intranasally administration, or parenterally, e.g. via injection.

For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA composition can assume a variety of states. In some examples, the composition is at least partially crystalline, uniformly crystalline, and/or anhydrous (e.g., less than 80, 50, 30, 20, or 10% water). In another example, the iRNA is in an aqueous phase, e.g., in a solution that includes water, this form being the preferred form for administration via inhalation.

The aqueous phase or the crystalline compositions can be incorporated into a delivery vehicle, e.g., a liposome (particularly for the aqueous phase), or a particle (e.g., a microparticle as can be appropriate for a crystalline composition). Generally, the iRNA composition is formulated in a manner that is compatible with the intended method of administration.

An iRNA preparation can be formulated in combination with another agent, e.g., another therapeutic agent or an agent that stabilizes an iRNA, e.g., a protein that complexes with iRNA to form an iRNP. Still other agents include chelators, e.g., EDTA (e.g., to remove divalent cations such as $Mg^{21}$), salts, RNAse inhibitors (e.g., a broad specificity RNAse inhibitor such as RNAsin) and so forth.

In one embodiment, the iRNA preparation includes another iRNA agent, e.g., a second iRNA agent that can mediate RNAi with respect to a second gene. Still other preparations can include at least three, five, ten, twenty, fifty, or a hundred or more different iRNA species. In some embodiments, the agents are directed to the same virus but different target sequences. In another embodiment, each iRNA agents is directed to a different virus. As demonstrated in the Example, more than one virus can be inhibited by co-administering two iRNA agents simultaneously, or at closely time intervals, each one directed to one of the viruses being treated.

Treatment Methods and Routes of Delivery

A composition that includes an iRNA agent of the present invention, e.g., an iRNA agent that targets RSV or PIV, can be delivered to a subject by a variety of routes. Exemplary routes include inhalation, intrathecal, parenchymal, intravenous, nasal, oral, and ocular delivery. The preferred means of administering the iRNA agents of the present invention is through direct administration to the lungs and nasal passage or systemically through parental administration.

An iRNA agent can be incorporated into pharmaceutical compositions suitable for administration. For example, compositions can include one or more iRNA agents and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, intranasal, transdermal, intrapulmonary), oral or parenteral. Parenteral administration includes intravenous drip, subcutaneous, intraperitoneal or intramuscular injection, or intrathecal or intraventricular administration.

In general, the delivery of the iRNA agents of the present invention is done to achieve delivery into the subject to the site of infection. The preferred means of achieving this is through either a local administration to the lungs or nasal passage, e.g. into the respiratory tissues via inhalation or intranasal administration, or via systemic administration, e.g. parental administration.

Formulations for inhalation or parenteral administration are well known in the art. Such formulation may include sterile aqueous solutions which may also contain buffers, diluents and other suitable additives. For intravenous use, the total concentration of solutes should be controlled to render the preparation isotonic.

The active compounds disclosed herein are preferably administered to the lung(s) or nasal passage of a subject by any suitable means. Active compounds may be administered by administering an aerosol suspension of respirable particles comprised of the active compound or active compounds, which the subject inhales. The active compound can be aerosolized in a variety of forms, such as, but not limited to, dry powder inhalants, metered dose inhalants, or liquid/liquid suspensions. The respirable particles may be liquid or solid. The particles may optionally contain other therapeutic ingredients such as amiloride, benzamil or phenamil, with the selected compound included in an amount effective to inhibit the reabsorption of water from airway mucous secretions, as described in U.S. Pat. No. 4,501,729.

The particulate pharmaceutical composition may optionally be combined with a carrier to aid in dispersion or transport. A suitable carrier such as a sugar (i.e., lactose, sucrose, trehalose, mannitol) may be blended with the active compound or compounds in any suitable ratio (e.g., a 1 to 1 ratio by weight).

Particles comprised of the active compound for practicing the present invention should include particles of respirable size, that is, particles of a size sufficiently small to pass through the mouth or nose and larynx upon inhalation and into the bronchi and alveoli of the lungs. In general, particles ranging from about 1 to 10 microns in size (more particularly, less than about 5 microns in size) are respirable. Particles of non-respirable size which are included in the aerosol tend to deposit in the throat and be swallowed, and the quantity of non-respirable particles in the aerosol is preferably minimized. For nasal administration, a particle size in the range of 10-500 uM is preferred to ensure retention in the nasal cavity.

Liquid pharmaceutical compositions of active compound for producing an aerosol may be prepared by combining the active compound with a suitable vehicle, such as sterile pyrogen free water. The hypertonic saline solutions used to carry out the present invention are preferably sterile, pyrogen-free solutions, comprising from one to fifteen percent (by weight) of the physiologically acceptable salt, and more preferably from three to seven percent by weight of the physiologically acceptable salt.

Aerosols of liquid particles comprising the active compound may be produced by any suitable means, such as with a pressure-driven jet nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation.

Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, preferably made isotonic, but may be hypertonic with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate therapeutic aerosol generator. Aerosol generators for administering solid particulate therapeutics to a subject produce particles which are respirable and generate a volume of aerosol containing a predetermined metered dose of a therapeutic at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

A second type of illustrative aerosol generator comprises a metered dose inhaler. Metered dose inhalers are pressurized aerosol dispensers, typically containing a suspension or solution formulation of the active ingredient in a liquefied propellant. During use these devices discharge the formulation through a valve adapted to deliver a metered volume, typically from 10 to 200 ul, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidant and suitable flavoring agents.

Administration can be provided by the subject or by another person, e.g., a caregiver. A caregiver can be any entity involved with providing care to the human: for example, a hospital, hospice, doctor's office, outpatient clinic; a healthcare worker such as a doctor, nurse, or other practitioner; or a spouse or guardian, such as a parent. The medication can be provided in measured doses or in a dispenser which delivers a metered dose.

The term "therapeutically effective amount" is the amount present in the composition that is needed to provide the desired level of drug in the subject to be treated to give the anticipated physiological response. In one embodiment, therapeutically effective amounts of two or more iRNA agents, each one directed to a different respiratory virus, e.g. RSV and PIV, are administered concurrently to a subject.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

Dosage. An iRNA agent can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmole of RNA agent (e.g., about 4.4×1016 copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight. The unit dose, for example, can be administered by injection (e.g., intravenous or intramuscular, intrathecally, or directly into an organ), an inhaled dose, or a topical application.

Delivery of an iRNA agent directly to an organ (e.g., directly to the liver) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ.

The dosage can be an amount effective to treat or prevent a disease or disorder.

In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities.

In one embodiment, a subject is administered an initial dose, and one or more maintenance doses of an iRNA agent, e.g., a double-stranded iRNA agent, or siRNA agent, (e.g., a precursor, e.g., a larger iRNA agent which can be processed into an siRNA agent, or a DNA which encodes an iRNA agent, e.g., a double-stranded iRNA agent, or siRNA agent, or precursor thereof). The maintenance dose or doses are generally lower than the initial dose, e.g., one-half less of the initial dose. A maintenance regimen can include treating the subject with a dose or doses ranging from 0.01 µg to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the iRNA agent pharmaceutical composition includes a plurality of iRNA agent species. The iRNA agent species can have sequences that are non-overlapping and non-adjacent with respect to a naturally occurring target sequence, e.g., a target sequence of the RSV gene. In another embodiment, the plurality of iRNA agent species is specific for different naturally occurring target genes. For example, an iRNA agent that targets the P protein gene of RSV can be present in the same pharmaceutical composition as an iRNA agent that targets a different gene, for example the N protein gene. In another embodiment, the iRNA agents are specific for different viruses, e.g. RSV and PIV.

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107,094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an iRNA agent, e.g., a double-stranded iRNA agent, or siRNA agent (e.g., a precursor, e.g., a larger iRNA agent which can be processed into an siRNA agent, or a DNA which encodes an iRNA agent, e.g., a double-stranded iRNA agent, or siRNA agent, or precursor thereof) can include a single treatment or, preferably, can include a series of treatments. It will also be appreciated that the effective dosage of an iRNA agent such as an siRNA agent used for treatment may increase or decrease over the course of a particular treatment. Changes in dosage may result and become apparent from the results of diagnostic assays as described herein. For example, the subject can be monitored after administering an iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target RSV RNA. The transgenic animal can be deficient for the corresponding endogenous RNA. In another embodiment, the composition for testing includes an iRNA agent that is complementary, at least in an internal region, to a sequence that is conserved between the target RSV RNA in the animal model and the target RSV RNA in a human.

The invention is further illustrated by the following examples, which should not be construed as further limiting.

EXAMPLES

Designing Antiviral siRNAs Against RSV and HPIV3 Phosphoprotein mRNA siRNA against RSV P and siRNAs against HPIV3 P mRNA were synthesized chemically (Bitko, V. & Barik, S. *BMC Microbiol.* 1, 34 (2001)) and their IC50 (concentration of siRNA producing 50% reduction of target) ex vivo was determined (FIG. 1a). The siRNA sequences and IC50 values are listed (Table 1). Two siRNAs against RSV-P (#1, #2) and one against HPIV3 (#4) showed appreciable inhibitory activities, and were selected for further study. The correlation of target mRNA with protein, as exemplified for siRNA #1 (FIG. 1a), agreed with an RNAi mechanism, and as we shown below, the knockdown activity of a siRNA ex vivo also matched with its activity in the animal (in vivo). Thus, the ex vivo assay provides a reliable, inexpensive, quick and convenient initial screening for an antiviral siRNA drug.

Intranasal (IN) siRNAs Inhibit RSV and HPIV3 Replication in Mouse Lung

To determine if the siRNAs that are active ex vivo would be effective during an actual infection, an animal model was used. The BALB/c mouse is a well-established laboratory model for RSV infection to study the progression, pathology, and immunology of the disease (Graham, B. S., et al., *J. Med. Virol.* 26, 153-162 (1988), van Schaik, S. M., et al., *J. Infect. Dis.* 177, 269-276 (1998), Haeberle, H. A. et al. *J. Virol.* 75, 878-890 (2001)). Mice were treated with siRNA complexed with TransIT-TKO® reagent intranasally, and 4 hr later challenged each animal with $10^7$ pfu of RSV or HPIV3, also intranasally. Maximal RSV growth in murine lung could be observed around 5-6 days p.i and this time point was used in further studies. siRNAs that were effective ex vivo (FIG. 1a) were highly antiviral in the animal (FIG. 1b,c). At a dose of 5 nmole IN siRNA (averaging ~70 ug for double-stranded siRNAs) per mouse, siRNA #1 and siRNA #4 respectively reduced pulmonary RSV and HPIV3 titer by about 5,000- and 100-fold in individual infections (FIG. 1b,c). Importantly, siRNAs, free of transfection reagents, also significantly inhibited pulmonary viral titers (FIG. 1d). This demonstrates that inhalation based anti-viral therapy is possible with simple pharmaceutical compositions comprising an iRNA agent. It is to be noted that HPIV3 does not infect the mouse as readily as RSV (Durbin, A. P., Elkins, W. R. & Murphy, B. R. *Vaccine* 18, 2462-2469 (2000)), which is the reason for the relatively lower HPIV3 replication in the mouse lung (FIG. 1c). Use of sucrose-purified high-titer HPIV3 as inoculum enabled the model to achieve measurable infections in the mouse lung.

Several additional features of the Example are applicable to various embodiments of the present invention. First, the results demonstrate the virus-specific effect of the siRNAs (FIG. 1). Even the most potent anti-RSV siRNA (#1) only inhibited RSV but not HPIV3, and vice versa, which alone argues against a nonspecific antiviral effect of the IN siRNA. Second, anti-luciferase siRNA (Elbashir, S. M. et al. *Nature* 411, 494-498 (2001)), even at the highest dose tested (50 nmole or 700 µg/mouse) did not inhibit either virus (FIGS. 1b-d). Finally, IN siRNAs with or without the Transit-TKO reagent in uninfected mice caused no obvious discomfort (as judged by normal coat, activity, appetite and weight gain, and lack of any respiratory distress), suggesting a favorable pharmacology for potential drug development.

It should be noted that in all experiments described herein, the results of viral protein immunoblot always matched with viral titer, and therefore, for a given experiment each can serve as a redundant marker of the other and all complementary data is not presented.

Specific Antiviral Effects of IN siRNA Prevent Lung Infection

Figure 2:
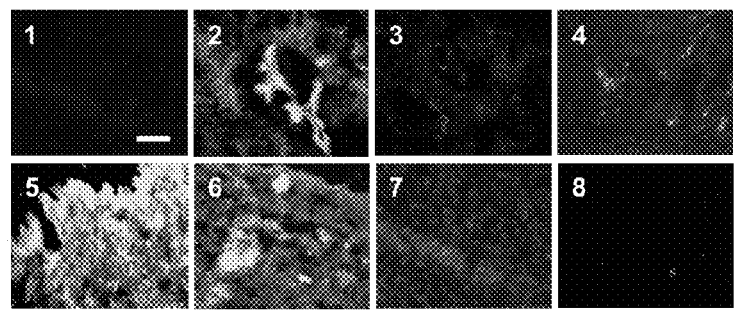
FIG. 2. Knockdown of viral antigens in siRNA-treated murine lung without IFN activation. (a) Virus was administered 4 hrs after siRNA, and viral antigens were detected by indirect immunohistology of lungs at 4 days p.i. (green, RSV; red, HPIV3). (1) sham-infected, probed with RSV P antibody; (2-6) RSV-infected, probed with RSV P antibody; (7,8) HPIV3-infected, probed with HPIV3 antibody. The following siRNAs (5 nmoles, ~70 ug)) were used: (1,2) none; (3) siRNA #1 plus TransIT-TKO reagent; (4) siRNA #1, no reagent; (5) negative control siRNA plus TransIT-TKO; (6) luc-siRNA plus TransIT-TKO; (7) none; (8) siRNA #4 plus TransIT-TKO. Representative lung tissues were at 5 days p.i. Bar=400 um. (b) Antisense strand of siRNA #1 was detected by Northern analysis of varying amounts of total lung RNA at 2 days after siRNA administration using labeled RSV P DNA as probe. A probe against RSV NS1 did not react, showing specificity of detection. (c) IN siRNA (10 nmole or 140 ug per mouse) did not activate pulmonary IFN of either type I (IFN-$\alpha$) or type II (IFN-$\gamma$) above the threshold of detection (~10 pg/ml), whereas in control lungs, RSV-infection activated type II and low levels of type I. Lanes: 1, siRNA #1; 2, siRNA #4; 3, Luc siRNA; 4, no siRNA but RSV-infected (with error bar shown). Lungs were obtained 2 days after siRNA administration and 4 days after infection (n=4 for each graph). (d) siRNA-mediated inhibition of dual infection by RSV and HPIV3 determined by indirect immunohistology (green, RSV; red, HPIV3). (1, 5) no siRNA; (2, 6) siRNA #1, 5 nanomole (70 ug); (3, 7) siRNA #4, 5 nanomole (70 ug); (4, 8) siRNA #1 and siRNA #4, 5 nanomole each. (1-4) probed with RSV P antibody; (5-8) probed with HPIV3 antibody. Virus was administered 4 hrs after siRNA, and lung tissues were examined at 4 days p.i. Bar=400 um.
Figure 2:
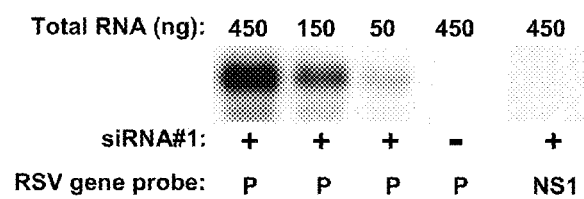
Figure 2:
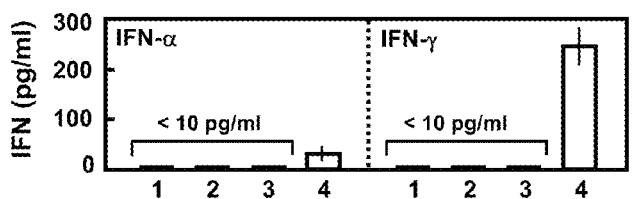
Figure 2:
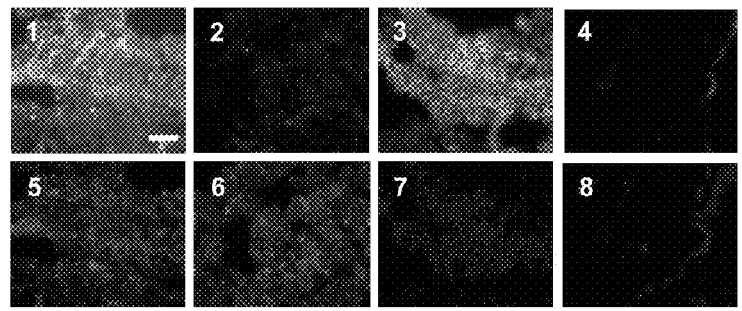

Although the results presented above documented inhibition of viral replication, they did not directly prove abrogation of infection of the lung tissue. We, therefore, probed various sections of both lungs at 5 days p.i. using antibodies specific for the appropriate virus. With $10^7$ pfu instilled per mouse, both viruses produced robust pulmonary infection. In representative results (FIG. 2a), infection was strongly abolished in mice pre-treated with 5 nmole (70 ug) of anti-RSV siRNA #1 complexed with TransIT-TKO. Similar reduction of HPIV3 infection was also seen with 5 nmole anti-HPIV3 siRNA #4. As with viral titer, siRNA without transfection reagent showed significant reduction of infection, as represented for RSV. For the same amount of siRNA, we estimate that the reagent-free siRNA was roughly 70-80% as effective as siRNA complexed with TransIT-TKO. Although we have only presented data for TransIT-TKO-complexed siRNA in the rest the paper, these results point to the exciting prospect that IN delivery of pure naked siRNA, free of other chemicals, may offer substantial protection against respiratory pathogens. This is particularly important as transfection reagents themselves may have side-effects. We note here that polyethyleneimine (PEI) has been successfully used as a carrier for intravenous (IV) as well as intratracheal (IT) delivery of siRNA and DNA against influenza virus (Ge, Q., et al., *Proc. Natl. Acad. Sci. USA* 101, 8676-8681 (2004)). However, in our experience, direct IN administration of PEI, with or without siRNA, often resulted in overt sickness and/or death of the mouse.

IN siRNAs Locate to the Lung and do not Activate Interferon

To provide further evidence that the viral inhibition observed in the lung was a direct and specific effect of the nasally applied siRNA, two kinds of experiments were performed. First, we were able to detect the antisense strand of the siRNA in the lung tissue (FIG. 2b) by specific Northern analyses. Second, the possibility that the antiviral effect of siRNAs was due to activation of interferons (IFNs) was ruled out by the following. Paramyxoviruses in general encode diverse mechanisms to counteract IFNs; RSV, in particular, is largely resistant to type I IFNs (IFN-α/β) although sensitive to type II IFN (IFN-γ) (Schlender, J., et al., *J. Virol.* 74, 8234-8242 (2000), Ramaswamy, M., et al., *Am. J. Respir. Cell Mol. Biol.* 30, 893-900 (2004)). Our early studies showed that the siRNAs were active against RSV and HPIV3 in Vero cells that contain deletions of type I IFN genes (data not shown). Nonetheless, we measured the levels of IFN-α and IFN-γ in murine lung tissues at different days following treatment with various siRNAs, and found no activation of either type of IFN (FIG. 2c).

siRNAs Competitively Protect Against RSV and HPIV3 in Mixed Infection

Co-infection of the respiratory tract by multiple agents is always a possibility, and in some studies joint infection by RSV and HPIV3 has been diagnosed (Coiras, M. T., et al, *J. Med. Virol.* 72, 484-495 (2004)). In fact, chimeric viruses and recombinant vaccines incorporating RSV as well HPIV3 antigens have been constructed with the hope that they would offer simultaneous protection against both viruses (Schmidt, A. C., et al., *J. Virol.* 75, 4594-4603 (2001), Bernhard, W. et al. *Am. J. Respir. Cell Mol. Biol.* 25, 725-731 (2001)). The specific antiviral effect of siRNA #1 and siRNA #4 against RSV and HPIV3, respectively, prompted us to test them together (5 nmole or 70 ug of each) in mixed infection of the mice by both viruses. Control mice were treated with a single kind of siRNA (either #1 or #4). As there is no easy way to determine the pfu of each virus in a mixture of the two, we resorted to immunofluorescence microscopy as described above, and subjected the lung tissue sections to dual staining using a mixture of anti-RSV and anti-HPIV3 antibodies. Mixed infection of the lung tissue was indeed achieved by this criterion (FIG. 2d). In mice pre-treated with either siRNA #1 or siRNA #4, RSV and HPIV3 infection respectively was prevented, as seen by the loss of either green or red fluorescence, but not both (FIG. 2d). Using a combination of the two siRNAs (5 nmole, i.e., 70 ug of each) both types of fluorescence disappeared, documenting the inhibition of both viruses (FIG. 2d). As before, the same siRNA mix without any transfection reagent was also highly active (data not shown).

Figure 3:
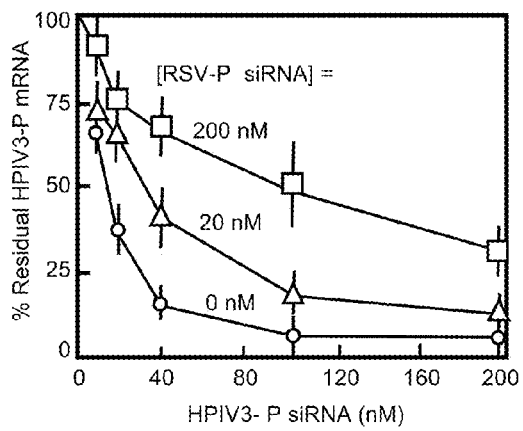
FIG. 3. Competitive viral inhibition at high siRNA concentration in dual infection by RSV and HPIV3. (a) Real-time PCR (ex vivo); (b) immunoblot (ex vivo); (c) pulmonary immunoblot with goat antiviral antibodies. The respective viral N protein band intensity was quantified and expressed as percentage of siRNA-untreated lung samples. Virus was administered 4 hrs after siRNA, and lung tissues were at 5 days p.i. (n=4 for each data point). Black bar, RSV; white bar, HPIV3. Standard errors are as shown.
Figure 3:
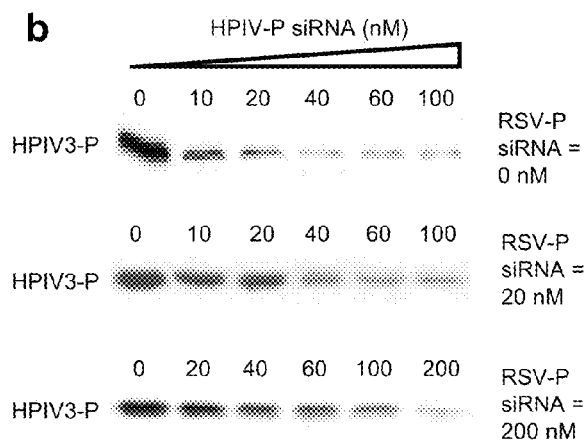
Figure 3:
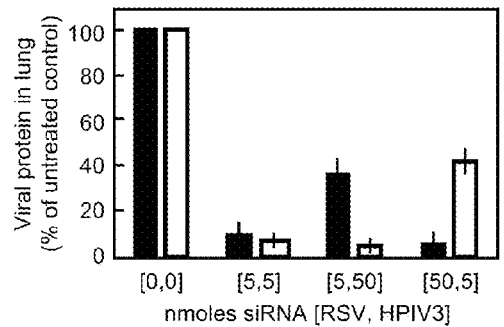

Interestingly, when excessively high amounts of one siRNA were used, the activity of the other siRNA was inhibited in a dual infection assay (FIG. 3). By quantitative real-time RT-PCR, the IC50 of siRNA #4 (against HPIV3 P) ex vivo increased through 15, 35 and 100 nM as the concentration of siRNA #1 (against RSVP) was raised from 0 to 20 to 200 nM (FIG. 3a). These results were validated by measurement of HPIV3 P protein in immunoblot (FIG. 3b). In dual infection of mice, immunoblot quantitation of N protein of each virus produced an essentially identical conclusion: whereas 5 nmole (70 ug) of each siRNA effectively inhibited both viruses, 50 nmole of one siRNA reduced the effect of 5 nmole of the other in a mutual manner (FIG. 3c).

IN siRNAs Prevent Pulmonary Pathology

Figure 4:
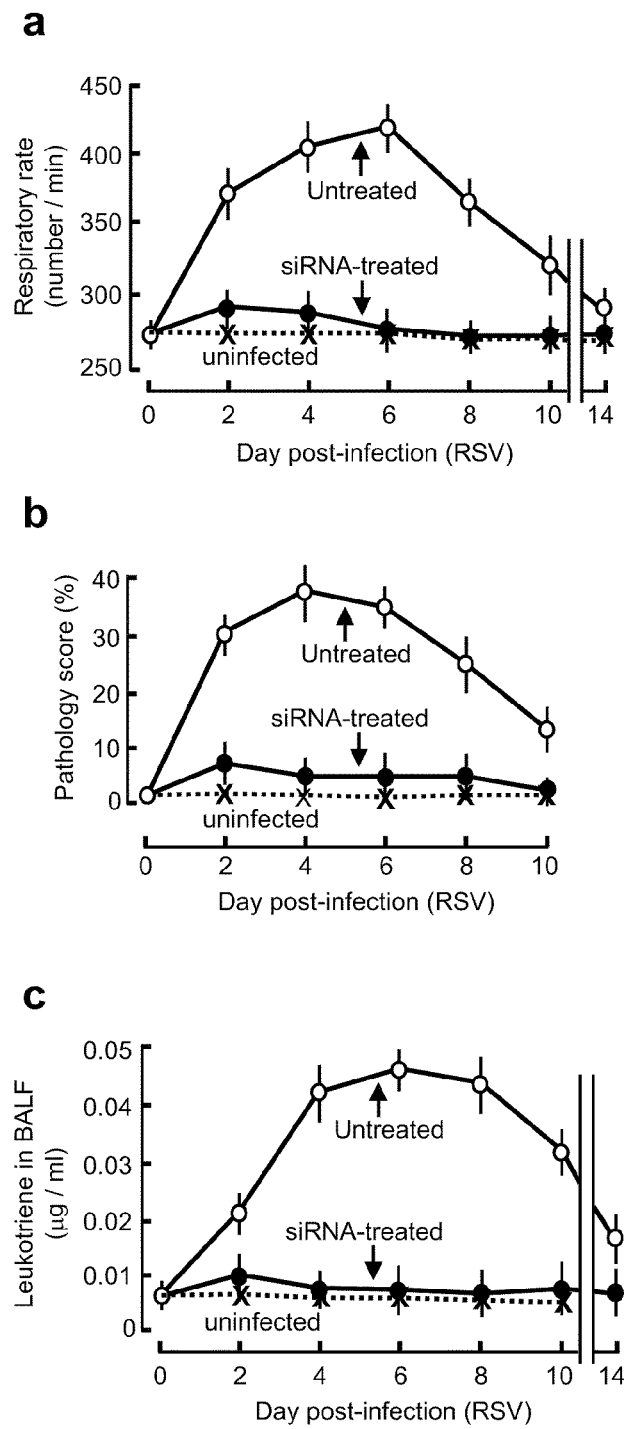
FIG. 4. Relief of lung pathology and reduction of an asthma marker in siRNA #1-treated mice. (a) Respiratory rate; (b) Pulmonary histopathology; (c) Leukotriene. P<0.002 in all assays; n=4 for all data points; standard error bars are shown. Virus was administered 4 hrs after siRNA (70 ug). Mice treated with negative control siRNA were indistinguishable from siRNA-untreated (data not shown).

Since the siRNAs prevented infection a logical query was whether they prevented the development of pathological features as well. Upon visual inspection the siRNA-treated RSV-exposed mice acted and appeared essentially like uninfected mice with normal activity, shiny coat and general well-being. We then measured the respiratory rate, induction of leukotriene, and pulmonary inflammation. Respiratory rate of BALB/c mice is known to increase in response to RSV infection (Haeberle, H. A. et al. *J. Virol.* 75, 878-890 (2001), Volovitz, B., et al., *Pediatr. Res.* 24, 504-507 (1988)). Leukotrienes, a product of the lipoxygenase pathway, bind to the leukotriene receptors present in bronchial smooth muscle and are elevated in the respiratory secretions of asthmatic patients, human infants with RSV infection, and mice infected with RSV (Volovitz, B., et al., *Pediatr. Res.* 24, 504-507 (1988), Welliver, R. C., 2nd, et al., *J. Infect. Dis.* 187, 1773-1779 (2003)). These compounds provoke airway mucus secretion, bronchoconstriction and airway infiltration by inflammatory cells, which are important hallmarks of severe RSV disease. When we administered anti-RSV siRNA #1 at the same time as (or prior to) RSV, a significant reduction in respiratory rate, pulmonary histopathology and leukotriene accumulation in bronchoalveolar fluid (BALF) was observed (FIG. 4). These values remained near baseline and were essentially comparable to those in sham-infected mice. All parameters remained low at least 14 days post-infection, demonstrating that the siRNA truly prevented illness and not just postponed it. In fact, siRNA-treated mice showed no visible signs of respiratory distress up to 6 weeks of observation. Negative control RNA or luc-siRNA (Table 1) offered no relief in all experiments (data not shown).

IN siRNAs are Effective Antivirals Post-Infection

Having shown that siRNAs can prevent respiratory viral disease if administered prior to infection, we asked the question whether they may have a curative effect once infection has established, as this is an important goal in pediatric medicine. In this series of experiments, we administered siRNA #1 at various days after RSV infection and the mice were weighed daily. Mice are known to lose weight up to about 8-10 days following RSV infection, after which they either die or slowly regain weight depending on whether the starting inoculum is too high or moderate-to-low (Haeberle, H. A. et al. *J. Virol.* 75, 878-890 (2001)). In a similar cohort of mice, the lungs were sampled on pre-determined days to assay for infectious virus. As expected, the siRNA-untreated mice maintained their body weight for about 4 days p.i., followed by a gradual loss that continued at least up to 9 days (FIG. 5a). Mice treated with siRNA prior to (data not shown) or at the same time as RSV (Day 0) essentially appeared uninfected and continued to gain weight without interruption. Most mice receiving siRNA on Day 1 were also quite hard to distinguish from the sham-infected controls. Those receiving siRNA at subsequent days (Day 1-4) showed gradually less and less protection, although significant improvement of weight was observed at all days for all treatments.

A similar picture emerged when pulmonary RSV titer was determined in these mice on Day 2, 4, 6, 8, 10, and 16 (FIG. 5b). In the siRNA-untreated mice, the titer rose till Day 4-5, and then slowly dropped to undetectable levels by Day 16. siRNA treatment before or concomitant to RSV infection held the titer 5,000-fold down at all days tested. Administration of siRNA at later times in infection was progressively less effective, but the viral titer was always lower than the untreated controls on any day tested. It appeared that the siRNA, no matter when it was administered, slowed down the rate of virus replication, resulting in a lower peak titer. Subsequently, the titer fell below detectable levels at earlier and earlier times the sooner the siRNA was administered. For example, whereas in the untreated infected mice pulmonary RSV could be detected up to about 16 days p.i., it could not be detected in the Day 1 siRNA-treated mice after 10 days p.i. As before, negative control siRNA or luciferase siRNA (Table 1) had no effect in all experiments (data not shown). Together, these results showed that the RSV P siRNA had a curative effect even when administered post-infection and that the mice were always less sick and recovered quicker than their untreated cohorts.

Discussion

The principal finding of this paper is that appropriately designed siRNAs, applied intranasally, offer protection from respiratory infection as well as provide significant therapy when applied post-infection. siRNAs, delivered by small particle aerosols in a simple hand-held inhaler, can be used to prevent or treat pulmonary infections. While our manuscript was in preparation, two reports appeared in which siRNAs inhibited influenza virus, another major respiratory pathogen, in a murine model (Ge, Q., et al., *Proc. Natl. Acad. Sci. USA* 101, 8676-8681 (2004), Tompkins, S. M., et al., *Proc. Natl. Acad. Sci. USA* 101, 8682-8686 (2004)). In one study (Ge, Q., et al., *Proc. Natl. Acad. Sci. USA* 101, 8676-8681 (2004)), synthetic siRNA or plasmid DNA expressing siRNA was administered via a combination of IV and IT routes. In the other study (Tompkins, S. M., et al., *Proc. Natl. Acad. Sci. USA* 101, 8682-8686 (2004)), siRNA was first delivered by hydrodynamic IV delivery; 16-24 hr later mice were infected with influenza virus and given a second dose of siRNA in a lipid carrier, both via IN route. Presence of pulmonary virus was tested 2 days later and a 10-50 fold inhibition was observed with different strains of influenza virus. Our studies against RSV and PIV offer the following improvement and simplification over the previous ones: (i) The delivery is solely intranasal and therefore, relatively noninvasive and painless, making it amenable to an inhaler or mist-based therapy. (ii) siRNA without any carrier is significantly effective, thus reducing the potential risk of side effects of the carrier. (iii) A single dose of about 5 nanomole siRNA (70 ug of double-stranded RNA) appears to provide benefit over the full duration of infection. A more comprehensive screening of the target sequence (e.g., RSV P) and use of newer chemistry may lead to siRNAs with significantly lower IC50 and better pharmacokinetics, resulting in a lower dosage. siRNAs exhibit various degrees of non-specific, off-target effects, especially at high concentrations (Jackson, A. L. et al. *Nat. Biotechnol.* 21, 635-637 (2003), Sledz, C. A., et al., *Nat. Cell Biol.* 5, 834-839 (2003), Persengiev, S. P., et al., *RNA* 10, 12-18 (2004), Bridge, A. J., et al., *Nat. Genet.* 34, 263-264 (2003)). This is an obvious concern in therapy, and IV administration of siRNA may result in systemic side-effects. In contrast, the intranasally delivered siRNA is more likely to be concentrated—if not exclusively localized—in the respiratory tissues, thus minimizing the side effects. Lack of IFN activation by intranasally delivered synthetic siRNA supports and extends previous finding that chemically synthesized siRNAs, devoid of 5' phosphates, do not activate the IFN pathway in cell culture (Kim, D. H. et al. *Nat. Biotechnol.* 22, 321-325 (2004)). Together, correlation of antiviral activity with specific mRNA knockdown (FIG. 1), detection of the siRNA in the target tissue (lung) (FIG. 2*b*), lack of IFN activation (FIG. 2*c*), and virus-specific effect of the siRNAs (FIGS. 1-3)—all provide evidence that the antiviral effect is specific, directed and is RNAi-mediated. (iii) Respiratory viruses, such as RSV and PIV, exhibit high selectivity in tissue tropism in infecting the respiratory tissues. Thus, IN delivery ensures that the siRNA is targeted to the site of infection—an ideal condition for pharmacology.

Although RSV and HPIV sometimes co-infect, their interactions have remained largely ignored. The exact reason behind the observed inhibition of one siRNA by another needs further study. The fact that it also happens ex vivo (cell culture) argues against, although does not rule out, humoral factors and cytokines in the animal, such as interferon. RSV actually inhibits interferon activation (Schlender, J., et al., *J. Virol.* 74, 8234-8242 (2000), Ramaswamy, M., et al., *Am. J. Respir. Cell Mol. Biol.* 30, 893-900 (2004)), and thus, should facilitate rather than inhibit PIV growth. Another possibility is that growth of one virus inhibits the other through other mechanisms, such as competition for intracellular resources. On the other hand, it is known that the RNAi machinery in a cell is saturable and thus two siRNAs could potentially compete for a fixed pool of this machinery (Batik, S. *Virus Res.* 102, 27-35 (2004), (Hutvagner, G., et al., *PLoS Biol.* 2, E98 (2004)). It is to be noted that such competition was only appreciable at relatively high doses of the siRNAs, i.e., with tens or hundreds of nanomoles (FIG. 3). In contrast, only a few nanomoles of our siRNAs offered nearly complete protection in mice. Thus, the observed competition is not a matter of practical concern with siRNAs of IC50 in the low nanomolar range.

Figure 5:
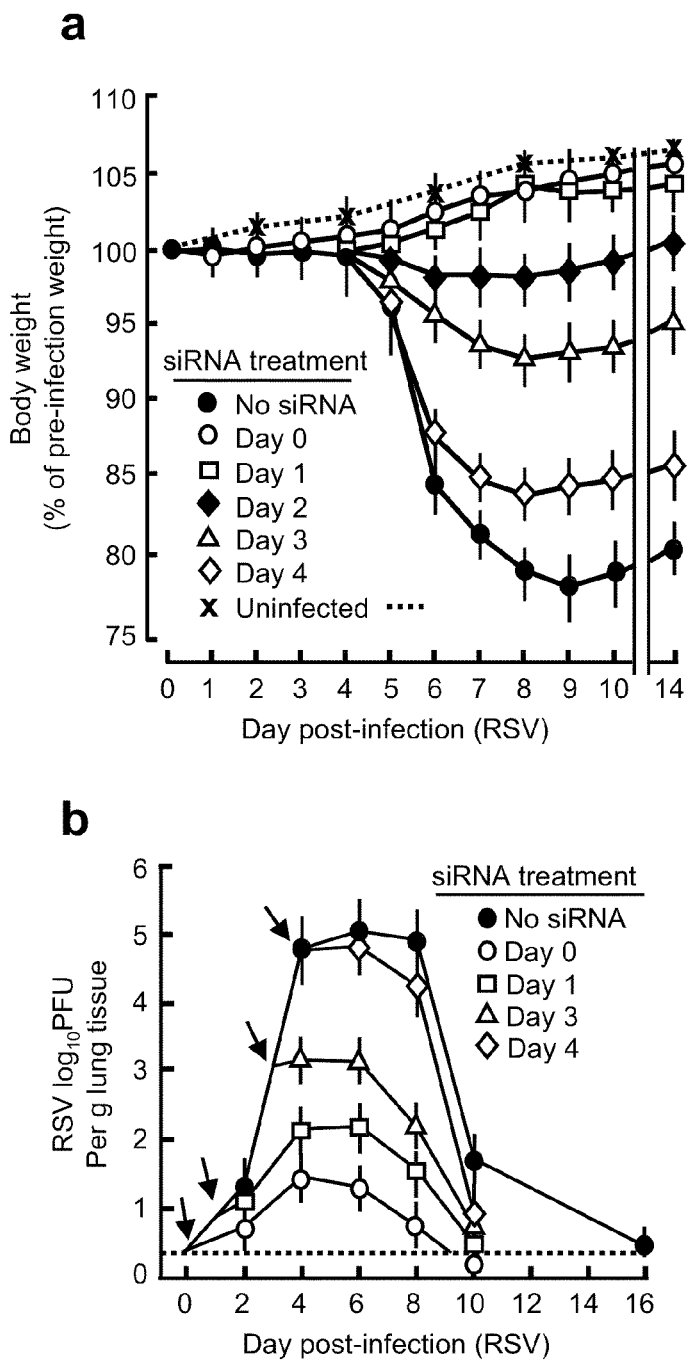
FIG. 5. Therapeutic effect of siRNA in RSV disease. Changes in (a) body weight and (b) pulmonary viral titer during RSV infection in mice. Standard error bars are shown; n=6 for each data point. The arrows indicate the day of siRNA (70 ug) administration.

When used as a prophylactic, the siRNA not only prevented the infection but also inhibited the appearance of various aspects of the disease process as measured by body weight, pulmonary pathology, respiratory parameters and allergy markers (FIG. 4). The kinetics of the disease process in mice and men are relatively similar and in both species immunopathological changes occur rapidly following RSV infection. When used as a treatment drug after infection ensued, the siRNAs are not expected to correct the pathology that has already occurred. Even then, however, inhibition of further growth of the virus resulted in a quicker cure and recovery (FIG. 5). Thus, it seems that the "window of opportunity" of treatment exists at all times in the RSV-infected patient although, as in any disease, earlier treatments should produce better prognosis. The effectiveness of the naked siRNA remains to be explained. It is possible that the respiratory tissue, especially the lung, is naturally more receptive to the exchange of small molecules, or perhaps becomes so when infected.

Lastly, depending on the stringency of siRNA-target pairing, exposure to siRNA may cause selection of siRNA-resistant viruses, and this has been demonstrated in HIV (Das, A. T. et al. *J. Virol.* 78, 2601-2605 (2004)). We have not faced this problem so far with the siRNAs tested here. The viruses that could be recovered from the siRNA-treated murine lung were grown in A549 cell culture and found to exhibit the same IC50 for the siRNA as the original inoculum (data not shown). Moreover, sequencing of the siRNA region of the P gene in six such independent plaque-purified RSV isolates revealed the wild type parental sequence (data not shown). Even if occasional resistance is encountered in the future, a second siRNA with a low IC50 and targeting a different region of the P mRNA or a different viral mRNA can be used in a multidrug regimen, thereby reducing the odds of viral resistance.

Methods

Virus, siRNA and other reagents. RSV Long strain and human PIV type 3 (HPIV3) JS strain were grown on HEp-2 monolayers as described for RSV (Burke, E., et al., *Virology* 252, 137-148 (1998), Burke, E., et al., *J. Virol.* 74, 669-675 (2000), Gupta, S., et al., *J. Virol.* 72, 2655-2662 (1998)). The extracellular media containing liberated progeny virus was collected at about 70 h for RSV and 50 h for HPIV3. The viruses were purified and concentrated by precipitation with polyethylene glycol (MW 8,000) and sucrose gradient centrifugation essentially as described for RSV (Ueba, O. *Acta. Med. Okayama* 32, 265-272 (1978)). The final preparations had infectious titers in the range of $10^8$-$10^9$ pfu/ml and were stored frozen at $-80°$ C. in small portions. All infectious viral titers (pfu) were determined by agarose plaque assay on HEp-2 monolayers with neutral red staining (Burke, E., et al., *Virology* 252, 137-148 (1998), Burke, E., et al., *J. Virol.* 74, 669-675 (2000), Gupta, S., et al., *J. Virol.* 72, 2655-2662 (1998)).

siRNAs were purchased from Dharmacon and processed as recommended by the manufacturer (Bitko, V. & Barik, S. *BMC Microbiol.* 1, 34 (2001). The TransIT-TKO® reagent was from Mims Bio Corp (Madison, Wis.). RSV-P antibody, raised in rabbit, was used in all immunohistological staining (Bitko, V. & Barik, S. *BMC Microbiol.* 1, 34 (2001). Polyclonal RSV and HPIV3 antibodies were raised against purified virions in goat and purchased from Chemicon (Temecula, Calif.) and BiosPacific (Emeryville, Calif.), respectively; the nucleocapsid protein (N) is the major viral band detected by these antibodies in immunoblot. Profilin antibody has been described (Burke, E., et al., *J. Virol.* 74, 669-675 (2000), Gupta, S., et al., *J. Virol.* 72, 2655-2662 (1998)).

Virus infection and siRNA treatment. Infection and siRNA treatment of A549 cells grown in monolayers were carried out as described (Bitko, V. & Barik, S. *BMC Microbiol.* 1, 34 (2001)). Intranasal application of RSV in mice is an established procedure and causes bronchiolitis. Pathogen-free 8-10 week old female BALB/c mice, weighing between 16 and 20 g) were purchased from Charles River Laboratories. Anesthesia for infection or siRNA administration was achieved with intraperitoneal injection of 0.2 ml of nembutal (5 mg/ml). Euthanasia was carried out by cervical dislocation following anesthesia with 0.3 ml nembutal. The siRNA was appropriately diluted in the dilution buffer provided by the manufacturer so that the desired amount is contained in 1 ul. This was mixed with 5 ul of the TransIT-TKO® reagent and 35 ul of Opti-MEM (Gibco Life Technologies, Invitrogen, Carlsbad, Calif.) immediately before experiment to produce a total volume of 41 ul. When siRNA was used without carrier, the 5 ul transfection reagent was substituted with 5 ul of Opti-MEM. The sucrose-purified virus was appropriately diluted in cold phosphate-buffered saline (PBS) immediately prior to infection such that $10^7$ pfu virus was contained in 30 μl. Sham infection was performed with the same volume of virus-free PBS. Both the siRNA mix and the virus were equally divided into the two nostrils and applied with a micropipette (i.e., each nostril received 35 ug siRNA in 20.5 ul and $0.5 \times 10^7$ pfu virus in 15 ul). No special equipment was needed as the mice inhaled all fluid through natural breathing. For dual infection, RSV and HPIV3 stocks were diluted such that each mouse was given a mixture of $10^7$ pfu of each virus and a mixture of 5 nmole (70 ug) each of siRNA #1 and siRNA #4 in the same volumes as before. Animal experiments obeyed all prescribed guidelines and were approved by the IACUC.

Pulmonary viral assay and clinical measurements. The animals were checked daily and weighed. Standard RSV symptoms were noted, including nasal mucus, increased respiratory rate due to congestion and bronchiolitis, a dull coat, ruffled fur and/or loss of fur, and a general lethargy and malaise. Respiratory rates (breaths per min) were determined by video recording (Volovitz, B., et al., Pediatr. Res. 24, 504-507 (1988)). Sneezing, sniffing and sighing were excluded from counting. At various days post-infection (p.i.), lungs were removed for RSV detection by infectious virus assay, immunoblot analysis, or immunostaining, as described below.

To determine viral titer, the lung was homogenized in DMEM supplemented with 2% FBS (2 ml DMEM per 100 mg tissue) in cold. The extract was centrifuged at 2,000×g for 10 min, and serial dilutions of the supernatant were assayed for pfu. For immunoblot of viral proteins (Burke, E., et al., Virology 252, 137-148 (1998)), 10 ul of the homogenized sample (before centrifugation) was added to 10 ul of 2×SDS-PAGE sample buffer, the mixture heated at 98° C. for 5 min, clarified by centrifugation in a microfuge at room temperature, and 10 ul of the clear supernatant analyzed by immunoblot using goat anti-RSV and anti-HPIV3 antibodies. To measure IFN (Durbin, J. E. et al. J. Immunol. 168, 2944-2952 (2002)), the lungs were homogenized in PBS, processed as above, and serial dilutions were assayed by ELISA kits (R&D Systems, Minneapolis, Minn.) having detection limits of 10 pg/ml.

For pulmonary histopathology, lungs were perfused and fixed in 10% buffered formalin and embedded in paraffin. Multiple, 4 μm thick sections were stained with haematoxylin & eosin and scored for cellular inflammation under light microscopy by two independent researchers. Inflammatory infiltrates were scored by enumerating the layers of inflammatory cells surrounding the vessels and bronchioles. Zero to three layers of inflammatory cells were considered normal, whereas more than three layers of inflammatory cells surrounding 50% or more of the circumference of the vessel or bronchioles were considered abnormal. The number of abnormal perivascular and peribronchial spaces divided by total such spaces was the percentage reported as the pathology score. A total of about 20 spaces per lung were counted for each animal. With $10^7$ RSV (and no siRNA) (Haeberle, H. A. et al. J. Virol. 75, 878-890 (2001)), about 30-35% of perivascular and peribronchial spaces could be found abnormal as early as Day 1 and peaked at around Day 5.

For immunohistology (Haeberle, H. A. et al. J. Virol. 75, 878-890 (2001)), the lung tissue was embedded in 100% OCT compound, and frozen at −80° C. Sections were cut onto slides, air-dried, fixed in acetone, were washed in PBS and permeabilized with 0.2% Triton X-100 in PBS, blocked for 20 min with 10% goat serum in PBS at room temperature. After multiple washes in PBS the tissue was incubated for 2 h at room temperature with either anti-RSV-P or anti-HPIV3 antibody diluted in PBS containing 1.5% goat serum. The slides were again washed multiple times in PBS, and the two antibodies were detected with FITC-conjugated anti-rabbit and TRITC-conjugated anti-goat immunoglobulin G antibody. After 1 h incubation at room temperature, the slides were given a final wash in PBS, mounted with the DABCO-DAPI mounting media and viewed by fluorescence microscopy (Bitko, V. & Barik, S. BMC Microbiol. 1, 34 (2001)).

Bronchoalveolar lavage fluid (BALF), was collected by perfusing the bronchi and the lungs with 5×1.0 ml normal saline (containing 10 ug indomethacin per ml) (Bernhard, W. et al. Am. J. Respir. Cell Mol. Biol. 25, 725-731 (2001)); total recovery of BALF per mouse was 4.2-4.4 ml. Samples containing visible signs of blood contamination were discarded. Cells were removed from BALF by centrifugation at 5,000×g for 15 min at 4° C., and samples stored at −80° C. until further analyses. The concentration of cysteinyl leukotrienes conjugates in the BALF was determined by an ELISA kit following the manufacturer's protocol (R&D Systems, Minneapolis, Minn.). According to the product insert, the cross-reactivity of the kit to the various leukotrienes was: LTC4 100%, LTD4 115%, LTE4 63% and LTB4 1.2%.

For Real Time PCR experiments, RNA was isolated from HPIV3-infected cells and the first-strand cDNA made using the GeneAmp RNA PCR Core kit (Perkin-Elmer Applied Biosystems, Foster City, Calif.). Primers are designed by the Beacon Designer software v 2.13 from Premier Biosoft. The following primers were used to amplify HPIV3 P mRNA: 5'-GGTCATCACACGAATGTACAAC-3' (SEQ ID NO: 1) and 5'-CTTGGAACATCTGCAGATTGTC-3' (SEQ ID NO:2). Real-time PCR was performed on the iCycler iQ Quantitative PCR system from BioRad Laboratories (Hercules, Calif.) using the iQ Sybr Green SuperMix. Gene expression measurements were calculated using the manufacturer's software and GAPDH as the internal control.

The antisense strand of siRNA in the lung was extracted and detected by Northern hybridization essentially as described (Reinhart, B. J., et al., Genes & Dev. 16, 1616-1626 (2002)) using complementary synthetic oligodeoxynucleotide terminally labeled with $^{32}P$.

Statistical analysis. Changes between treatment groups or between sets of in vitro experiments were analyzed by one-way ANOVA and then by Student's t test with Bonferroni correction. Increases in leukotriene concentrations were determined by the Mann-Whitney test. All numerical data were collected from at least 3 separate experiments. Results were expressed as mean±SEM (error bars in graphs). Differences were considered to be significant at P<0.05.

TABLE 1 siRNA sequences

| Name | Target | siRNA sequence | SEQ ID NO: | IC50 (nM) |
|---|---|---|---|---|
| siRNA #1 | RSV-P | 5'-CGAUAAUAUAACUGCAAGAdTdT-3' | (SEQ ID NO: 3) | 18 |
|  |  | 3'-dTdTGCUAUUAUAUUGACGUUCU-5' | (SEQ ID NO: 4) |  |
| siRNA #2 | RSV-P | 5'-CCCUACACCAAGUGAUAAUdTdT-3' | (SEQ ID NO: 5) | 80 |
|  |  | 3'-dTdTGGGAUGUGGUUCACUAUUA-5' | (SEQ ID NO: 6) |  |
| siRNA #3 | RSV-P | 5'-GAUGCCAUGAUUGGUUUAAdTdT-3' | (SEQ ID NO: 7) | >300 |
|  |  | 3'-dTdTCUACGGUACUAACCAAAUU-5' | (SEQ ID NO: 8) |  |
| siRNA #4 | HPIV3-P | 5'-CGAGUUGUAUGUGUAGCAAdTdT-3' | (SEQ ID NO: 9) | 15 |
|  |  | 3'-dTdTGCUCAACAUACACAUCGUU-5' | (SEQ ID NO: 10) |  |

TABLE 1-continued siRNA sequences

| Name | Target | siRNA sequence | SEQ ID NO: | IC50 (nM) |
|---|---|---|---|---|
| siRNA #5 | HPIV3-P | 5'-GAUAGACUUCCUAGCAGGAdTdT-3'<br>3'-dTdTCUAUCUGAAGGAUCGUCCU-5' | (SEQ ID NO: 11)<br>(SEQ ID NO: 12) | >300 |
| Luc-siRNA | Luciferase | 5'-CGUACGCGGAAUACUUCGAdTdT-3'<br>3'-dTdTGCAUGCGCCUUAUGAAGCU-5' | (SEQ ID NO: 13)<br>(SEQ ID NO: 14) | — |
| Negative | | 5'-UUCUCCGAACGUGUCACGUdTdT-3'<br>3'-dTdTAAGAGGCUUGCACAGUGCA-5' | (SEQ ID NO: 15)<br>(SEQ ID NO: 16) | — |

The GenBank accession numbers for RSV-P, HPIV3-P and luciferase sequences are M22644, Z11575 and X65324 respectively. Note that the siRNA sequences were based on actual sequencing of the viral strains in our laboratory; thus, siRNA #2 differs by one nucleotide from the GenBank sequence (the underlined C is U in M22644). Negative control siRNA sequence was from Qiagen (Valencia, Calif.).

What is claimed is:

1. A method of reducing the levels of a parainfluenza virus protein, parainfluenza virus mRNA, or parainfluenza virus titer in a cell in a subject comprising the step of administering an iRNA agent to said subject, wherein the iRNA agent comprises a sense strand having at least 15 contiguous nucleotides complementary to gene P from parainfluenza virus and an antisense strand having at least 15 contiguous nucleotides complementary to said sense strand, wherein said antisense strand comprises 15 or more contiguous nucleotides from a sequence consisting of nucleotides 1 to 19 of SEQ ID NO: 10.

2. The method of claim 1, wherein said sense strand comprises 15 or more contiguous nucleotides of a sequence consisting of nucleotides 1 to 19 of SEQ ID NO: 9.

3. The method of claim 1, wherein the subject is diagnosed as having a parainfluenza virus infection.

4. The method of claim 1, wherein said iRNA agent is administered intranasally to said subject.

5. The method of claim 1, wherein said iRNA agent is administered via inhalation or nebulization to said subject.

6. The method of claim 1, wherein said iRNA agent reduces the parainfluenza virus titer in said subject.

7. The method of claim 1, wherein said iRNA agent further comprises a non-nucleotide moiety.

8. The method of claim 1, wherein the sense and antisense strands are stabilized against nucleolytic degradation.

9. The method of claim 1, wherein at least one nucleotide of at least one strand is a 2'-modified nucleotide.

10. The method of claim 9, wherein said 2'-modified nucleotide comprises a modification selected from the group consisting of: 2'-methoxyethyl, 2'-OCH3, 2'-O-allyl, 2'-C-allyl, and 2'-fluoro.

11. The method of claim 9, wherein said 2'-modified nucleotide further comprises one or more phosphate linker modifications.

12. The method of claim 1, wherein said sense strand and said antisense strand comprise 1 to 4 deoxythymidine residues at their 3' end.

13. The method of claim 1, wherein said antisense strand and said sense strand are each 19 to 24 nucleotides in length.

14. The method of claim 13, wherein the antisense strand consists of SEQ ID NO: 10 and the sense strand consists of SEQ ID NO: 9.

15. An iRNA agent comprising a sense strand and an antisense strand, wherein said sense strand comprises at least 15 contiguous nucleotides complementary to gene P from parainfluenza virus and an antisense strand having at least 15 contiguous nucleotides complementary to said sense strand, wherein said antisense strand comprises 15 or more contiguous nucleotides from a sequence consisting of nucleotides 1 to 19 of SEQ ID NO: 10.

16. The iRNA agent of claim 15, wherein said sense strand comprises 15 or more contiguous nucleotides from a sequence consisting of nucleotides 1 to 19 of SEQ ID NO: 9.

17. The iRNA agent of claim 15, further comprising a non-nucleotide moiety.

18. The iRNA agent of claim 15, wherein the sense and antisense strands are stabilized against nucleolytic degradation.

19. The iRNA agent of claim 15, wherein at least one nucleotide of at least one strand is a 2'-modified nucleotide.

20. The iRNA agent of claim 19, wherein said 2'-modified nucleotide comprises a modification selected from the group consisting of: 2'-methoxyethyl, 2'-OCH$_3$, 2'-O-allyl, 2'-C-allyl, and 2'-fluoro.

21. The iRNA agent of claim 19, wherein said 2'-modified nucleotide further comprises one or more phosphate linker modifications.

22. The iRNA agent of claim 15, wherein said sense strand and said antisense strand comprise 1 to 4 deoxythymidine residues at their 3' end.

23. The iRNA agent of claim 15, wherein the antisense strand consists of SEQ ID NO: 10 and the sense strand consists of SEQ ID NO: 9.

* * * * *